United States Patent [19]
Collins et al.

[11] Patent Number: 6,160,166
[45] Date of Patent: Dec. 12, 2000

[54] PHOSPHONATED AGENTS AND THEIR ANTIANGIOGENIC AND ANTITUMORIGENIC USE

[75] Inventors: Delwood C. Collins; Antonio R. Gagliardi, both of Lexington, Ky.; Peter Nickel, Bonn, Germany

[73] Assignee: The University of Kentucky Research Foundation, Lexington, Ky.

[21] Appl. No.: 09/357,925

[22] Filed: Jul. 21, 1999

Related U.S. Application Data

[60] Division of application No. 09/121,124, Jul. 23, 1998, which is a continuation-in-part of application No. 08/899,996, Jul. 24, 1997, abandoned.

[51] Int. Cl.[7] ................................................ C07F 9/38
[52] U.S. Cl. .............................. 562/16; 562/20; 562/23; 562/24; 562/11; 562/16
[58] Field of Search .................................. 562/8, 11, 15, 562/16, 20, 23, 24

[56] References Cited

U.S. PATENT DOCUMENTS

| | | |
|---|---|---|
| 3,920,733 | 11/1975 | Birum . |
| 4,372,894 | 2/1983 | Helgstrand . |
| 4,719,297 | 1/1988 | Henne ..................................... 544/107 |
| 4,840,659 | 6/1989 | Franz ...................................... 504/201 |
| 5,652,227 | 7/1997 | Teronen . |
| 5,670,493 | 9/1997 | Cordi . |

FOREIGN PATENT DOCUMENTS

WO 95/23806   9/1995   WIPO .

OTHER PUBLICATIONS

CA;110:107683 abs of Chemotheraphy (Basel) by Strid 35(1) pp. 69–76, 1989.
Beilstein (BRN) 3946113 abs of Tetrahedron Lett by Sekine pp. 3013–3016, 1979.
CA:114:143709 abs of PL 150087, Apr. 1990.
CA:80:4935 abs of JP48006174, Feb. 1973.
CA:78:43620 abs of J Org Chem by Isbell 37(25) pp. 4399–4401, 1972.
CA:112:36035 abs of J Am Chem Soc by Swamy et al 112(1) pp. 223–228, 1990.
"Synthesis and Analytics of Phosphonic Acid Analogues of Suramin and Other Phosphoric Acid Derivatives, Potential Chemotherapeutics Against Filariasis" Dissertation by Mathias Huber, Freie University Berlin, 1982.
Klaus Dieter Jensch, et al. "Inhibition of Human Immunodeficiency Virus Type I Reverse Transcriptase by Suramin-–related Compounds," J. gen. Virol. (1987), vol. 68, pp. 2183–2192.
Reinhard Oesterle, et al. "Chemical modifications of aminoaphthalenesosulphanate acid derivatives increase effectivity and specificity of reverse transcriptase inhibition and change mode of action of reverse transcriptase and DNA polymerase alpha inhibition," Antiviral Research (1993) vol. 22, pp. 107–119.
Angela Firsching, et al. "Antiproliferative and Angiostatic Activity of Seramune Analogues," Cancer Research, vol. 55, Nov. 1, 1995, pp. 4957–4961.
CA:82:4363 abs of Z Anorg Allg Chem by Issleib, K., 408(3), 1974, pp. 266–274.
CA:107:190405 abs of J Gen Virol by Jentsch, K., 68(8), 1987, pp. 2183–2192.
CA:120:182336 abs of Antiviral Res by Oesterle R., 22(2–3), 1993, pp. 107–119.
CA:124:44745 abs of Cancer Res by Firsching A., 55(21), 1995, pp. 4957–4961.
CA:77:34992 abs of Sin. Fiz–Khim Polim., by Bakhitov M., No. 8, 1971, pp. 36–41.
STN on line filed Marpat accession No. 128:271686 abstract of CN 1125239, Jun. 26, 1996.
CA:107:190405 abstract of Jentschh, J. Gen. Virol.., 1987, 68(8), pp. 2183–2192
Firsching et al., "Antiproliferative and Angiostatic Activity of Suramin Analogues[1]", Nov. 1, 19951, Cancer Research 55, 4957–4961.
Sola et al., "Antitumor activity of FCE 26644 a new growth–factor complexing molecule", Cancer Chemother Pharmcol (1995) 36:217–222.
Ciomei et al., "New Sulfonated Distamycin a Derivatives with bFGF Complexing Activity", Biochemical Pharmacology, vol. 47, No. 2, pp. 295–302, 1994.
Database Carplus on STN, Chemical abstracts (Columbia, Ohio), CA No. 126:157635, Cordi et al., "Preparation of aminophenylphosponic acid derivatives, pharmaceutical compositions containing them and their angiogenesis inhibitor activity", abstract EP 754693 A2, Jan. 22, 1997.

*Primary Examiner*—Jean F Vollano
*Attorney, Agent, or Firm*—McDermott, Will & Emery

[57] ABSTRACT

Phosphonic acid agents are synthesized and characterized which are potent inhibitors of angiogenesis, tumorigenesis and metalloproteinase activity. Their method of use for the inhibition of angiogenesis and metalloproteinase and the treatment of tumors is also shown.

10 Claims, No Drawings

PHOSPHONATED AGENTS AND THEIR ANTIANGIOGENIC AND ANTITUMORIGENIC USE

CROSS REFERENCE TO RELATED APPLICATION

This application is a divisional of application Ser. No. 09/121,124 filed Jul. 23, 1998, which is a continuation-in-part of application Ser. No. 08/899,996 filed Jul. 24, 1997, now abandoned.

FIELD OF THE INVENTION

The present invention relates to phosphonic acid agents that are potent inhibitors of angiogenesis and tumorigenesis.

BACKGROUND ART

Angiogenesis is an essential component of tumor growth and metastasis. As reviewed by Folkman (1985), the growth of solid tumors is dependent on angiogenesis. Typically tumors do not grow beyond a size of 2–3 mm unless they are able to stimulate the growth of new capillaries from the existing vascular network. Additionally, the new blood vessels provide an essential entry route to the vasculature for metastasis of tumor cells. Cell division in endothelial cells is slow, with a turnover time of years rather than days or hours (Denekamp, 1984).

However, vascular endothelial cells undergo rapid proliferation with turnover times of a few days during the growth of new capillaries. Angiogenesis-dependent diseases such as diabetic retinopathy, psoriasis, arthritis, hemangiomas and tumor growth and metastasis are characterized by uncontrolled growth of capillary blood vessels. The most striking example of uncontrolled angiogenesis is associated with tumor growth (Folkman, 1985).

Accordingly, the search for angiogenesis inhibitors was stimulated by the concept of "antiangiogenic therapy". In its simplest terms, antiangiogenic therapy sought a putative inhibitor of blood vessel growth in the believe that such an inhibitor might be therapeutic by limiting tumor growth and further such an inhibitor would be non-toxic because angiogenesis is normally infrequent (Folkman, 1992). A number of different factors can stimulate angiogenesis in vivo. These angiogenic factors, such as basic fibroblast growth factor (bFGF), vascular endothelial growth factor (VEGF), platelet-derived growth factor (PDGF) and transforming growth factor α and β, can be released from the tumor cells themselves and by other cells such as macrophages and endothelial cells (Folkman, 1992).

The mechanisms by which tumors induce angiogenesis are very complex and involve many pathways, an angiogenesis inhibitor could be directed against any of the components of the angiogenic cascade. The identification of compounds that block neovascularization has a long standing interest. A number of inhibitory extracts have been prepared from avascular tissues, such as cartilage (Braunhut et al., 1989). One such method of treating tumors has been by the administration of suramin. However, it is believed that suramin may have adverse effects in large dosages.

Accordingly, a continuing need exists for agents that overcome the deficiencies of prior antiangiogenic compounds, including suramin. There is also a need for antiangiogenic agents that have a reduced toxicity to a recipient and increase inhibition of angiogenesis and tumorigenesis.

SUMMARY OF THE INVENTION

It is an object of the present invention to provide novel phosphonic acid substituted agents and pharmaceutical compositions containing said agents.

In an embodiment, the invention provides methods of treating tumors comprising the steps of administering an effective amount of a phosphonic acid substituted agent to a patient in need of said treatment.

In another embodiment the invention provides a method of inhibiting angiogenesis comprising the steps of administering an effective amount of a phosphonic acid substituted agent to a patient in need of said treatment.

In satisfaction of the foregoing objects and advantages, the present invention provides phosphonic acid derivatives of agents and methods for their preparation.

The invention also provides pharmaceutical compositions and methods for use of the compositions as potent inhibitors of angiogenesis and tumorigenesis.

In parent application Ser. No. 08/889,996, the compounds of the invention were referred to as naphthylureas. However, the more appropriate class of the agents are as described herein.

The above and other objects of the invention will become readily apparent to those of skill in the relevant art from the following detailed description, tables and formulas, wherein only the preferred embodiments of the invention are shown and described, simply by way of illustration of the best mode of carrying out the invention.

DESCRIPTION OF THE INVENTION

The present invention provides a novel group of phosphonic acid agents which were synthesized and characterized. This unique group of compounds are potent inhibitors of angiogenesis, equipotent to 40 times greater than suramin. In addition, results show that phosphonic acid agents demonstrate lower toxicity and exert their antiangiogenic effect via a different mechanism than suramin.

Without subscribing to any particular theory, it is believed that phosphonic acid agents are potent inhibitors of angiogenesis and that the antiangiogenic effect is mediated through a specific effect of these compounds upon proliferating endothelial cells. The mechanism for inhibition of angiogenesis by the phosphonic acid agents may involve inhibition of DNA replication, cell signaling and/or energy production.

Furthermore, the antiangiogenic and endothelial cell growth inhibiting activity of the phosphonic acid agents is not primarily related to the inhibition of binding of the angiogenic growth factors to their receptors on the endothelial cell surface as has been demonstrated for suramin.

The findings that this unique group of phosphonic acid agents have more potent antiangiogenic activity, are less toxic than suramin, and are metabolized and cleared in hours rather than weeks suggest that these agents are potent therapeutic agents for "angiogenesis-dependent" diseases. These diseases include diabetic retinopathy, arthritis, psoriasis, tumor growth and metastasis.

The commercial advantage of the phosphonic acid agents resides is their lower toxicity and enhanced antiangiogenic activity. The experiments presented illustrate the potent inhibition of angiogenesis by the use of the phosphonic acid agents to inhibit the growth of various immortalized human cancer cell lines. Further experiments provide in vivo mouse toxicity studies and neurotoxicity in vitro assays. Additionally, animal studies are presented in which SCID or nude mice are implanted with human tumors and then treated with the selected phosphonic acid agents.

According to the present invention, phosphonic acid agents, described by structural formula and chemical name, are potent inhibitors of angiogenesis and/or tumorigenesis while exhibiting low toxicity.

The present invention provides a preferred novel class of phosphonic acid group substituted agents which are defined by the following formulae:

$$(P-Y_{n1})_{m1}-Q^1-K-(Q^2-(Y_{n2}-P)_{m2})_j$$

wherein

P is a phosphonic group or a phosphonic salt, as for example, a phosphonic group substituted with one or more alkali metals;

Y is —OCO—, —NR$^1$CO—, or —CON(R$^1$)R$^2$—;

R$^1$ is H, CH$_2$CO$_2$H, or substituted or unsubstituted alkyl;

R$^2$ is substituted or unsubstituted alkyl, aryl, or arylalkyl;

Q$^1$ and Q$^2$ are substituted or unsubstituted aryl groups;

K is H, —NH—CO—NH—, —NH—CS—NH—, —NHCO—R$^3$—CONH—, or —NHCS—R$^3$—CSNH—; provided that when K is H, j is 0;

R$^3$ is a substituted or unsubstituted aryl group;

j is 0, 1, or 2;

n1 and n2 are independently 0, 1, or 2; and m1 and m2 are independently an integer from 1 to 4.

Embodiments of the phosphonic acid agents of the present invention comprise compounds of the formulae:

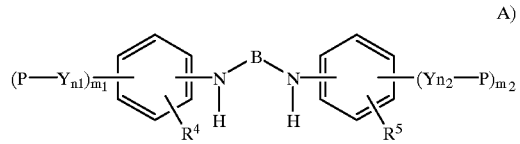
A)

or

B)

wherein

Y, P, n$_1$, n$_2$, m$_1$, m$_2$ R$^3$ are as defined above;

B is CO, CS, CO—R$^3$—CO, or CS—R$^3$—CS;

R$^4$ and R$^5$ are independently H or a substituted or unsubstituted alkyl group;

R$^6$ is H, or NCOR$^7$; and

R$^7$ is aryl, substituted aryl, or nitro substituted aryl.

Preferred phosphonic acid agents of the invention are set forth below in Tables 1–3, which tables provide chemical formulae, molecular weights, and properties of the compounds including some embryo and inhibition data.

TABLE 1

The code number, formula, molecular weight, synthesis method, basic structure and substitutions at positions 2, 3 and 4 for the phosphonic acid agents with small urea bridges are indicated.

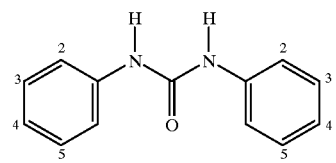

| | | | | Substitution at Position | | | # | % |
|---|---|---|---|---|---|---|---|---|
| Code | Formula | Mol Wt | Synthesis Method | -2 | -3 | -4 | Em | Ih |
| NF 158 | C$_{13}$H$_{12}$N$_2$O$_7$P$_2$Na$_2$ | 416.2 | B, C | H | PO$_3$HNa | H | 23 | 0 |
| NF 161 | C$_{13}$H$_{12}$N$_2$O$_7$P$_2$Na$_2$ | 416.2 | B, C | H | H | PO$_3$HNa | 21 | 53 |
| NF 473 | C$_{15}$H$_{12}$N$_2$O$_{11}$P$_2$Na$_2$ | 504.2 | G, B, C, Fb | OCOPO$_3$HNa | H | H | 20 | 21 |
| NF 426 | C$_{15}$H$_{12}$N$_2$O$_{11}$P$_2$Na$_2$ | 504.2 | G, B, C, Fb | H | OCOPO$_3$HNa | H | 22 | 39 |
| NF 392 | C$_{15}$H$_{12}$N$_2$O$_{11}$P$_2$Na$_2$ | 504.2 | G, B, C, Fb | H | H | OCOPO$_3$HNa | 24 | 6 |
| NF 474 | C$_{17}$H$_{16}$N$_2$O$_{11}$P$_2$Na$_2$ | 532.2 | G, B, C, Fb | H | CH$_3$ | OCOPO$_3$HNa | 21 | 12 |
| NF 427 | C$_{15}$H$_{14}$N$_4$O$_9$P$_2$Na$_2$ | 502.2 | Fa, Fb, B, C | H | NHCOPO$_3$HNa | H | | |
| NF 428 | C$_{15}$H$_{14}$N$_4$O$_9$P$_2$Na$_2$ | 502.2 | Fa, Fb, B, C | H | H | NHCOPO$_3$HNa | | |
| NF 433 | C$_{21}$H$_{22}$N$_4$O$_{13}$P$_2$Li$_2$ | 614.3 | A, B, C | H | Al | H | | |
| NF 434 | C$_{21}$H$_{22}$N$_4$O$_{13}$P$_2$Li$_2$ | 614.3 | | H | H | Al | | |

Where Em represents Embryos; Ih: represents Inhibition; and Al is

—CONCH$_2$PO$_3$HLi
|
CH$_2$CO$_2$H

TABLE 2

The code number, formula, molecular weight, synthesis method, basic structure and substitutions at positions 2, 3, 4, 4' and X for seven phosphonic acid agents with big urea bridges are indicated.

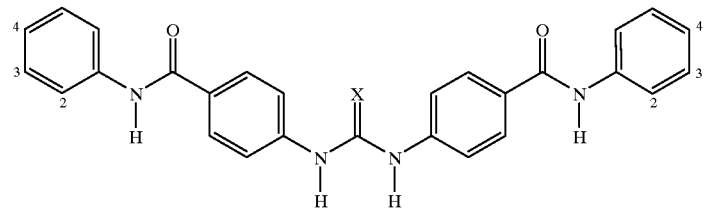

| Code | Formula | Mol Wt | Synthesis Method | Substitution at Position 3 | 4 | X | # Em | % Ih |
|---|---|---|---|---|---|---|---|---|
| NF 069 | C$_{27}$H$_{22}$N$_4$O$_9$P$_2$Na$_2$ | 654.4 | A, B, C, D | PO$_3$HNa | H | O | 26 | 66 |
| NF 681 | C$_{27}$H$_{22}$N$_4$O$_9$P$_2$Na$_2$ | 654.4 | A, B, C, D | H | PO$_3$HNa | O | 28 | 100 |
| NF 162 | C$_{27}$H$_{22}$N$_4$O$_8$P$_2$SNa$_2$ | 670.5 | A, B, C, D | H | PO$_3$HNa | S | | |

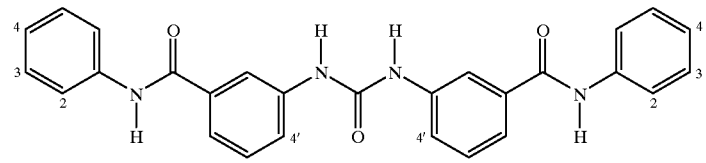

| Code | Formula | Mol Wt | Synthesis Method | Substitution at Position 2 | 3 | 4 | 4' | # Em | % Ih |
|---|---|---|---|---|---|---|---|---|---|
| NF 068 | C$_{27}$H$_{22}$N$_2$O$_9$P$_2$Na$_2$ | 654.4 | A, B, C, D | H | PO$_3$HNa | H | H | 27 | 0 |
| NF 067 | C$_{27}$H$_{22}$N$_2$O$_9$P$_2$Na$_2$ | 654.4 | A, B, C, D | H | H | PO$_3$HNa | H | 25 | 62 |
| NF 540 | C$_{31}$H$_{30}$N$_4$O$_9$P$_2$Na$_2$ | 710.5 | Ea, Ec, B, A, B, C | H | H | CH$_2$PO$_3$HNa | CH$_3$ | | |
| NF 544 | C$_{33}$H$_{38}$N$_4$O$_{15}$P$_4$ | 854.6 | Ea, Ec, B, A, B, C | CH$_2$PO$_3$H$_2$ | H | CH$_2$PO$_3$H$_2$ | CH$_3$ | | |

TABLE 3

The code number, formula, molecular weight, synthesis method, and chemical structures of phosphonic acid agents are indicated.

Synthesis Method | Compound

A

NF 166 C$_{12}$H$_{16}$N$_2$O$_8$P$_2$Na$_2$ (424.19)

TABLE 3-continued

The code number, formula, molecular weight, synthesis
method, and chemical structures of phosphonic acid agents are indicated.

| Synthesis Method | Compound |
|---|---|
| A, B, C | 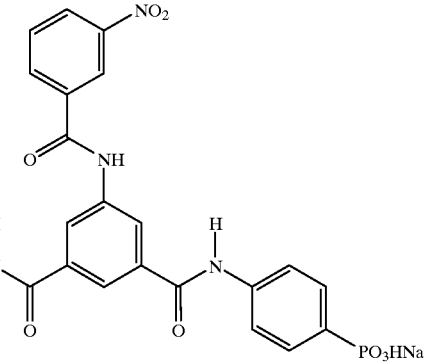<br>NF 167 $C_{27}H_{20}N_4O_{11}P_2Na_2$ (684.40) |
| A, B, A, B, C | 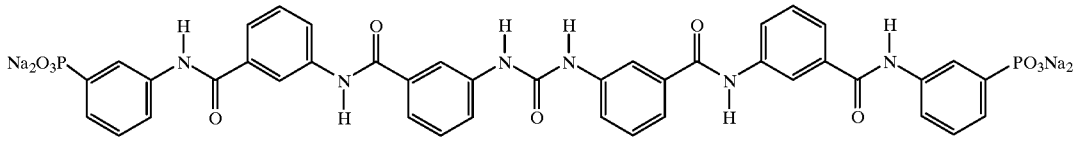<br>NF 050 $C_{41}H_{30}N_6O_{11}P_2Na_4$ (936.62) |
| A, B, A, B, C | 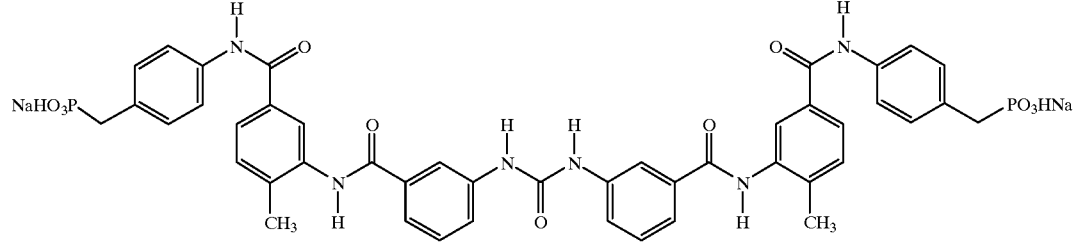<br>NF 542 $C_{45}H_{40}N_6O_{11}P_2Na_2$ (948.77) |

Synthesis of Phosphonic Acid Agents

The syntheses of the phosphonic acid agents of this invention are shown in process Schemes 1 and 2 below. General procedures for the syntheses are described under Synthetic Methods A–G. Synthetic methods used for the synthesis of the individual phosphonic acid agents are listed in Tables 2–3.

The phosphonic acid agents synthesized herein can be divided into three general groups. Table 1 shows phosphonic acid agents with small urea bridges. The basic structural formula, the chemical substitutions at each position, formula and molecular weight, are shown for each compound. The molecular weights of this group varied from 416 to 614 depending on the substitutions at positions 2, 3 and 4 of the basic structure. The basic structure of this group was synthesized using synthetic methods B and C described below (see structure for NF 158 and NF 161). Additional substitutions at positions 2, 3 and 4 were made using synthetic methods A, Fa, Fb and G as indicated in Table 1.

Table 2 shows seven phosphonic acid agents with large urea bridges. Two basic structural formulas with four benzene rings are shown with the chemical substitutions at each position, formula and molecular weights for each compound. The molecular weights of this chemical group varied from 698 to 855 depending on the substitutions at 2, 3, 4, 4' and X of the basic structures. The basic structures of this group were synthesized using synthetic methods A, B, C and D indicated below. (See NF 067, 068, 069 and 681). NF 540 and NF 544 required synthetic steps Ea and Ec instead of D.

Table 3 shows four phosphonic acid agents with miscellaneous structures. Because of differences in the basic structures of this group, the entire structure is shown with the formula and molecular weights. The molecular weights of this group varied from 424 to 949. NF 166 was synthesized using synthetic method A described below. NF 167 required synthetic method A, B and C, whereas NF 050 and NF 542 required synthetic method A, B, A, B and C.

Schemes 1 and 2 as set forth below show general procedures for preparation of the novel compounds of this invention. In Scheme 1, the phosphonic acid agents are prepared by initial reduction of a nitro benzene phosphonic acid to the amino derivative. This amino derivative is then reacted with a di-acid halide to yield the phosphonic acid substituted agent (e.g. compounds 4a, b). Such di-acid halides include phosgene, thiophosgene and a dicarboxylic acid halide substituted aryl group.

In an alternative embodiment, the amino derivative is reacted with a nitro benzoyl halide in a buffered medium and at temperatures of from about 20 to about 40° C. The nitrobenzoyl halide is added in an organic solvent such as toluene. At the conclusion of the reaction, the aqueous layer and organic layer are separated and the aqueous layer is acidified by the addition of a mineral acid from which a precipitated intermediate product, nitrobenzamido-benzenephosphonic acid, is recovered.

This nitrobenzamido-benzenephosphonic acid is then hydrogenated in the presence of a hydrogenation catalyst comprising a precious metal such as palladium or platinum on carbon to hydrogenate the nitro group and form an aminobenzamido-benzenephosphonic acid.

The aminobenzamido-benzenephosphonic acid is then dissolved in a buffered aqueous medium and treated with phosgene in an organic solvent to produce the final agent precipitated product. These reactions are described more specifically under Procedures A, B and C.

Scheme 1 General synthesis of the phosphonic acid substituted agents:

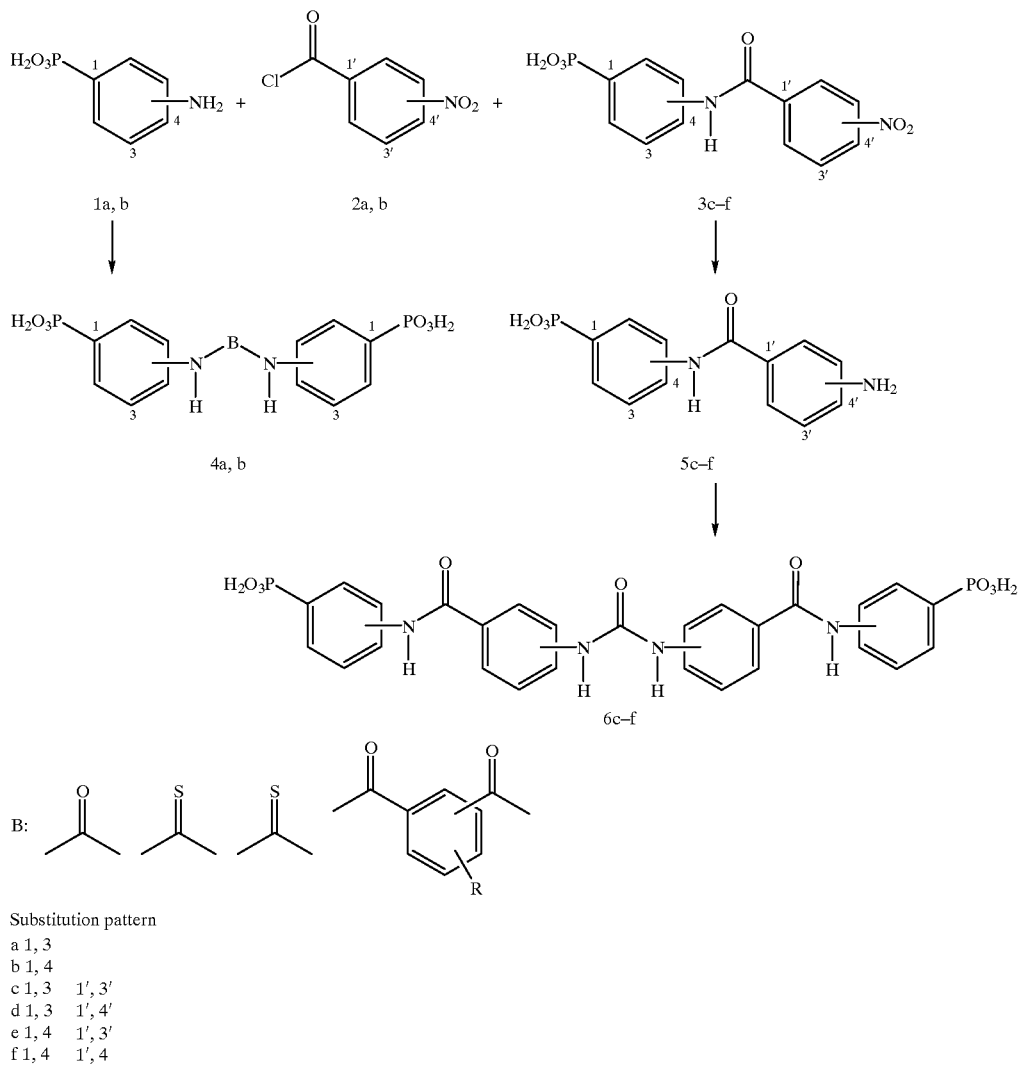

Scheme 2 sets forth a general synthesis for producing the various arylalkyl-, phenoxycarbonyl-, and carbamoyl-phosphonic acid analogues. In these reactions, the substituted benzene derivatives, compounds 11, 15 or 17 are reacted with the appropriate alkyl phosphite to form compounds 13, 16 and 18, respectively. These compounds will contain the appropriate substituents as shown in Scheme 2.

More specifically, the chloromethyl substituted benzene 12 is reacted with an alkyl phosphite by heating at about 80° C. up to reflux for 3 to 10 hours. The resulting 12 is then nitrated to 13. Compound 14 may then be produced from compound 13 by heating with concentrated hydrochloric acid and crystallizing the product.

In a further embodiment, the nitrophenoxy carbonylchloride 15 is reacted with an alkylphosphite in an exothermic reaction to produce a nitrophenoxycarbonyl-phosphonic acid dialkyl ester 16. This intermediate can be converted by reaction with sodium iodide in a solvent with an haloalkylsilane by heating at about 30° to about 50° C. to produce compound 19.

Alternatively, the nitrophenylisocyanate (compound 17) is reacted with a dialkylphosphite in an exothermic reaction to yield the phosphonic acid ester (compound 18). Thereafter, the phosphonic acid ester is reacted with trisodium iodide in a solvent and with an halotrialkylsilane by heating at about 30° to about 60° C. to produce compound 19. Compound 16 can be converted to compound 19 by the same procedure.

Scheme 2 General synthesis of arylalkyl-, phenoxycarbonyl-carbamoyl-phosphonic acid agents

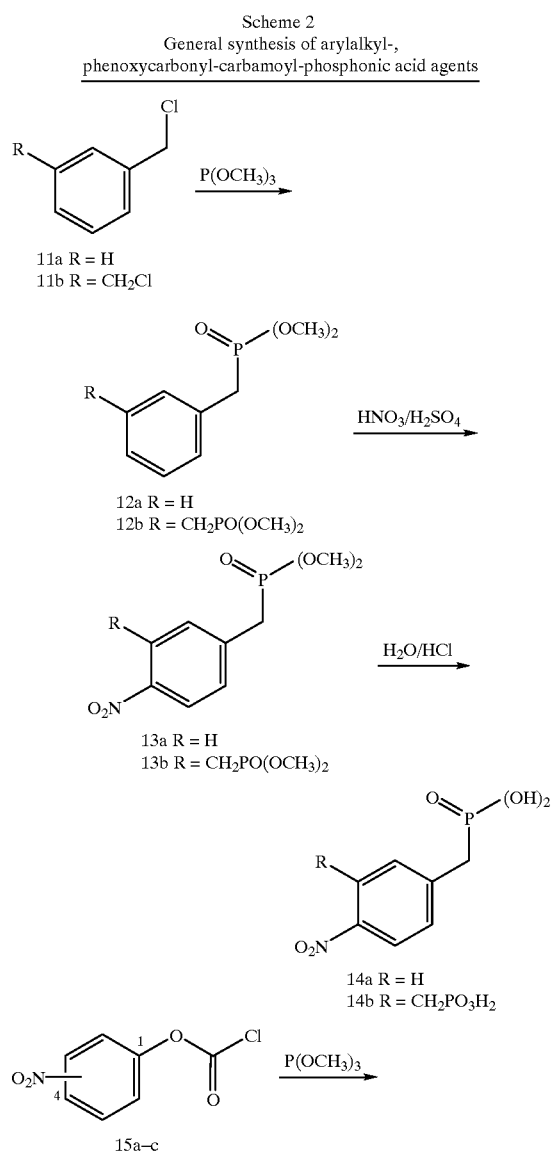

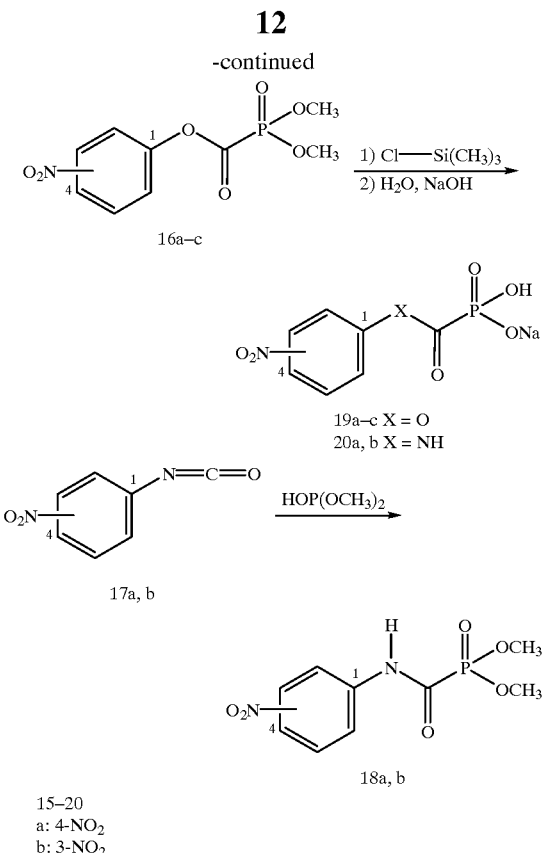

15–20
a: 4-$NO_2$
b: 3-$NO_2$
c: 2-$NO_2$

Synthetic Methods for Phosphonic Acid Agents

A. 4-(4-Nitrobenzamido)-benzenephosphonic acid (3f)

4-Aminobenzenephosphonic acid (1b) was prepared as described by Doak D. O. and Freedman C D, *J. Amer. Chem. Soc.*, 74, 753 (1952). Compound 1b (17.3 g, 0.1 mol) was dissolved in 2 N NaOH (100 ml). To this solution (pH 8), a solution of 4-nitrobenzoylchloride (2b, 30 g, 0.15 mol) in toluene (100 ml) was added dropwise at room temperature with vigorous stirring. Stirring was continued until no more 1b was detectable by TLC. Soon after the beginning of the addition of 4-nitrobenzoylchloride, 3f began to precipitate. NaOH (2 N) was added to the reaction mixture at a rate that kept 3f in solution. At the end of the reaction, the aqueous layer was pH 11. The toluene layer was separated. The aqueous layer was acidified to pH 1.0 by addition of concentrated hydrochloric acid and stirred for 30 min. The precipitate was filtrated and crystallized from methanol.

Yield 25.3 g (78%). Melting point: 257–260° C.

$C_{13}H_{11}N_2O_6P$ (322.4)

In a similar way a series of aminoaryl- or aminoalkyl-phosphonic acids was benzoylated using nitrobenzene-mono or di-carbonylchlorides.

B. 4-(4-Aminobenzamido)-benzenephosphonic acid (5f)

Compound 3f (8.05 g) was dissolved in a mixture of 1 M $Na_2CO_3$ (15 ml), water (55 ml) and methanol (30 ml) (pH 8.0) and hydrogenated at room temperature at normal pressure using 10% Pd/C (200 mg) as catalyst. After absorption of the theoretical amount of hydrogen (about 4 hr), the filtrate of the reaction mixture was concentrated to 70 ml and acidified with 2 N HCl to pH 6.0. The monosodium salt of compound 5f precipitated. It was washed with water and dried at about 40° C. $C_{13}H_{13}N_2O_4P$ (292.4); $C_{13}H_{12}N_2O_4PNa$ (314.4) monosodium salt of compound 5f.

In a similar way all aromatic nitro compounds used as intermediates were hydrogenated to the corresponding aromatic amino compounds.

C. 4,4'-[Carbonylbis(imino-4,1-phenylencarbonylimino)]-bis-benzenephosphonic acid (6f)

Compound 5f (5.85 g, 20) was dissolved in water (50 ml) and 5 M NaOH (4.0 ml). To this solution, a 20% solution (2 M, 50 ml, 100 nmol) of phosgene in toluene was added dropwise (4 hr) under vigorous stirring. During the whole reaction time, the pH of the reaction mixture was maintained at pH 5.0 by automatic addition of 5 M NaOH. A suspension was formed during the addition of phosgene. The toluene layer was separated. The aqueous suspension was acidified with 2 N HCl to pH 1 and stirred for 30 min. The precipitate was filtered by suction, stirred three times with water (20 ml, 30 min) and dried.

Yield: 3.6 g (61%)

$C_{27}H_{24}N_4O_9P_2$ (610.4)

In a similar way amino derivatives were reacted with a di-acid halide to yield the phosphonic acid substituted agent. A thiophosgene or a dicarboxylic acid halide was used to synthesize the corresponding agent.

D. Tetrasodium salt of compound 6f

Compound 3f (0.61 g 1.0 mol) was suspended in water (10 ml). The suspension was titrated very slowly with 0.1 N NaOH to pH 9.0. The resulting clear solution was evaporated i. vacuum to dryness.

$C_{27}H_{20}N_4O_9P_2Na_4$ (698.4)

TLC (Acetonitrile, $NH_3$ conc., water 6+2+2); compound 6f Rf 0.63; compound 5f Rf 0.75; compound 3f Rf 0.79; 4-Nitrobenzoic acid Rf 0.75; HPLC purity of compound 6f>96% determined by the method described by Kassack and Nickel (1996).

E. 4-Nitro-1,3-xylene-α,α-diphosphonic acid (14b)

a) 1,3-Bis-(chloromethyl)benzene (11b, 25 g, 0.1 mol) and triethyl phosphite (36.5 g, 0.22 mol) were heated under reflux for 10 hr.

b) The reaction mixture (12b, yellow oil) was cooled to room temperature and added dropwise to a mixture of conc. nitric acid (30 ml, 0.4 mol) and conc. sulfuric acid (30 ml) at about 0–5° C. After 2 hr, the reaction mixture was poured in ice water (500 ml) and extracted with toluene. The toluene extracts were washed with water and evaporated, yielding a yellow oil (13b).

c) Compound 13b was heated with conc. hydrochloric acid under reflux for 20 hr. The reaction mixture was evaporated. The residue was crystallized from water yielding yellow crystals of compound 14b (mp 172° C., 15.8 g, yield=50%).

In a similar way using steps a) and c) (4-nitrophenyl) methane phosphonic acid (14a) was synthesized starting from 4-nitro-α-chlorotoluene.

F. (3-Nitrophenyl)carbamoyl phosphonic acid monosodium salt (20b)

a) 3-Nitrophenylisocyanate ((17b) 0.82 g, 5 mmol) and dimethyl phosphite (0.55 g, 5 mmol) were mixed. Addition of two drops of triethylamine led to a spontaneous exothermic reaction. The reaction mixture was crystallized from methanol/ether yielding yellow crystals (0.44 g, 32%), mp 107° C. (3-nitrophenylcarbamoyl phosphonic acid dimethylester, 18b).

b) Compound 18b (5 mmol) and sodium iodide (10 mmol) were dissolved in acetonitrile (30 ml). Chlorotrimethylsilane (15 mmol) was added dropwise. The mixture was heated to about 40° C. for 30 min, cooled and filtrated. The filtrate was concentrated to a volume of 10 ml. Water (10 ml) was added and the pH of the solution was adjusted to pH 3 by addition of 0.1 N NaOH. The solution was extracted three times with ether (15 ml). The aqueous phase was freeze-dried, yielding an amorphous powder (20b).

G. 4-Nitrophenoxycarbonylphosphonic acid dimethylester (16a)

Trimethyl phosphite (4 ml, 30 mmol) was added dropwise under stirring and cooling to 4-nitrophenoxycarbonyl chloride (15a, 6.4 g, 32 mmol) (exothermic reaction). The reaction mixture was crystallized from ether/pentane yielding yellow crystals (16a, 6.8 g, 77%), mp 105° C.

In a similar way the 2-nitro- (16c) and 3-nitro- (16b) analogues were synthesized. (See also Doak G O and Freedman C D. *J. Amer. Chem. Soc.,* 74:753, 1952. Kassack M and Nickel P. *J. Chromatogr. B,* 686, 275–284, 1996, incorporated herein by reference in their entirety).

The basic structure of the molecules synthesized were similar to suramin. However, the trisulfonic acid derivatives were replaced with phosphonic acid groups ($PO_3HNa$) or (—O—CO—$PO_3HNa$) at the 2 (2'), 3 (3') or 4 (4') positions. These alterations resulted in lower molecular weights (414–950) compared to the molecular weight of suramin (1429) and other trisulfonic acid analogues (1162–1541). Both large urea and small urea phosphonic agents were synthesized. The chemical and pharmacological properties are very different from those described for other suramin analogues. The metabolic clearance rates of the phosphonic acid agents appear to be much faster (hours versus 45–55 days for suramin).

EXAMPLE 1

Pharmacological Activities: Antiangiogenic Activity in the Chick Chorioallantoic Membrane Assay In Vivo and the Human Microvascular Endothelial Cells In Vitro The purpose of this experiment was to test the ability of the phosphonic acid agents described above to inhibit angiogenesis. The ID50, the dose that produces 50% inhibition of angiogenesis, was determined for suramin and each of the phosphonic acid agents by measuring the ability of various doses to inhibit angiogenesis in vivo in the chick egg chorioallantoic membrane (CAM) assay as described by Gagliardi et al. 1992. Some of the phosphonic acid agents showed ID50 values significantly lower than suramin. Two phosphonic acid agents, NF 069 and NF 681, showed the lowest ID50 values (4–8 times more active than suramin). Six other phosphonic acid agents showed antiangiogenic activity that was 2 to 4 times greater than suramin (NF 050, NF 067, NF 161, NF 167 and NF 428). Other phosphonic acid agents were equipotent to suramin. These data clearly indicate the discovery of a group of unique phosphonic acid agents which show antiangiogenic activity that is up to 8 fold greater than suramin in the CAM assay.

It was also found that the compounds described above, in general, showed a closely related antiangiogenic activity on the growth of human dermal Microvascular endothelial cells stimulated by basic fibroblast growth factor (bFGF) in vitro. The IC50 values for those phosphonic acid agents were 22–80 μM compared to 438 μM for suramin. This indicates that these phosphonic acid agents are 5–40 times more potent inhibitors of endothelial cell growth than suramin in vitro.

EXAMPLE 2
Differences in the Effect of Suramin and the Phosphonic Acid Agents on Angiogenesis in the 6-Day Old and 11-Day Old CAM Assay According to Ausprunk et al. (1974), capillary angiogenesis in the CAM is completed by day 11. Measurements of intercapillary distances are also consistent with the cessation of capillary growth after day 10. Flamme et al. (1991) showed that CAM fluid contains angiogenic growth factors, that the mitogenic activity of these growth factors was temporally related to the vascular growth in the CAM, and that by day 10, there was a sharp decrease in growth factor activity in the CAM fluid which preceded the termination of capillary growth by one day. Based on these observations, the effect of suramin and some phosphonic acid agents on the established vessels of the CAM membrane after cessation of vascular growth was determined. The implants were prepared as previously described by Gagliardi et al. (1992), implanted on day 11 and read on day 13.

The results of this study showed that the phosphonic acid agents (NF 067, NF 069, NF 681) were very potent inhibitors of angiogenesis in the 6-day CAM and exhibited no significant inhibitory activity in the 11 day CAM (see Table 4). Suramin showed antiangiogenic activity in both the 6-day and 11-day CAMs.

This is a very important finding and suggests that the phosphonic acid agents are very potent inhibitors of angiogenesis during the phase of rapidly growing vessels in the CAM (6-day) but do not affect the established vasculature (11-day CAM). On the other hand, suramin clearly affected both the growing and established vascular cells. These results indicate that the mechanisms of action of suramin and the phosphonic acid agents on angiogenesis are different. Additional experiments compare the mechanisms of actions of the phosphonic acid agents on angiogenesis in vivo.

TABLE 4

Comparison of the inhibition of angiogenesis by 70 nmol of suramin or a equimolar amount of a phosphonic acid agents in the 6-day and 11-day chick egg chorioallantoic (CAM) assay.

| Analogues | Chemical Structure | 6-day CAM % Inhibition | 11-day CAM % Inhibition |
|---|---|---|---|
| suramin | | 64 | 50 |
| NF 068 | phosphonic | 0 | 0 |
| NF 067 | phosphonic | 63 | 0 |
| NF 069 | phosphonic | 68 | 0 |
| NF 681 | phosphonic | 100 | 0 |

EXAMPLE 3
Differences in the Inhibitory Effects of Suramin and the Phosphonic Acid Agents on bFGF-Stimulated and Non-Stimulated Endothelial Cells Suramin is a highly charged molecule with six sulfonate groups that are ionized at physiologic pH. This results in significant nonspecific binding to polypeptide growth factors (Coffey et al., 1987). However, suramin also exhibits specificity by binding to specific sites on a growth factor, similar to heparin binding to bFGF (Middaugh et al., 1992). While these studies showed that suramin is able to disrupt the binding of growth factors to their receptors in intact cells, it also has diverse effects on other key enzymes involved in signal transduction and mitogenesis that probably contribute to its antiproliferative and antimetastatic activities.

The data indicates that bFGF induced a dose-related increase in total protein and total DNA in human dermal microvascular and porcine pulmonary artery endothelial cells. The presence of suramin (210 μM) inhibited the stimulatory effect of bFGF, as has also been reported by Takano et al. (1994) and Braddock et al. (1994) for bovine aorta and bovine adrenal microvascular endothelial cells. In the presence of much lower concentrations (25 μM), the phosphonic agents, NF 050, NF 067, NF 069, NF 681, NF 161, NF 167 and NF 428, not only inhibited the stimulation of endothelial cell growth by bFGF but significantly reduced total protein content far below the unstimulated control endothelial cells. These exciting results show that the agents are much more potent inhibitors of endothelial cell growth than suramin and that mechanisms other than blocking growth factor binding to endothelial cells play a very important role in their antiangiogenic activity.

The results with suramin are similar to those reported in the literature (Takano et al., 1994 and Braddock et al., 1994) that suramin inhibited $I^{125}$ bFGF binding in a dose-related manner. However, the phosphonic agents in the same molar concentrations used for suramin did not affect either the total or the specific binding of the iodinated growth factor to the endothelial cells. The percentage of inhibition of I125 bFGF binding to low and high affinity binding sites of human microvascular endothelial cells was 96% at 70 μM of suramin, decreasing to 9% at 25 μM of suramin. However, for the same concentrations of the phosphonic acid agents, the inhibition of growth factor binding was always less than 5% in relation to the control. These data clearly show that we have identified a chemical group that are very potent as antiangiogenic agents and express their activity through different mechanisms than those widely accepted for suramin.

As described above, the phosphonic acid agents are very inhibitory in the actively growing vessels of the 6-day CAM but showed almost no activity on the established vessels of the 11-day CAM (see Table 2). When compared with the MTT assay confluent and low density cultures in log phase growth, the phosphonic acid agents are 10-fold more inhibitory for growing cultures than for confluent human microvascular endothelial cell cultures.

This in vitro finding corroborates our data with the CAM assay in different phases of growth, suggesting that this new class of phosphonic acid agents target growing blood vessels.

EXAMPLE 4
Differences in the Growth Inhibitory Effects of Suramin and the Phosphonic Acid Agents in Human Microvascular Endothelial Cells and Established Cancer Cell Lines in Culture We have investigated the activity of the phosphonic acid agents on some tumor cell lines proliferation in vitro and compared this activity with the antiangiogenic activity of these compounds in the CAM assay and their inhibitory activity in human microvascular endothelial cell growth.

The MTT assay (Carmichael et al., 1987) was used to examine the effects of suramin and selected phosphonic acid agents on cell proliferation. Suramin and the phosphonic acid agents inhibited cell proliferation in a dose-related manner. Analysis of the inhibitory action of the phosphonic acid agents in adrenal cortex carcinoma (SW13), human pancreatic adenocarcinoma (CFPAK-1), human prostate carcinomas (LNCap and PC3) showed IC50 equipotent or values less than suramin. In other cell lines, such as human breast carcinomas (MCF7 and T47D), human fibrosarcoma (HT1080), human colon adenocarcinoma (CaCo2), human glioblastoma (U87), kidney carcinoma (A498) and lung carcinoma (A427), the phosphonic acid agents showed IC50 values higher than suramin.

The phosphonic acid agents, NF 067 (which is 20 times more potent than suramin in inhibiting microvascular endothelial cell growth), expressed very low antiproliferative activity against different cancer cell lines in vitro. Our data and the reports in the literature strengthen our important finding that some of the phosphonic acid agents are more potent inhibitors of angiogenesis in the CAM assay and to human microvascular endothelial cell growth than suramin. This effect is not observed with some cancer cell lines. This suggests that there is specificity for endothelial cells in the inhibitory effect of the phosphonic acid agents not observed with suramin and the other trisulfonic acid analogues.

EXAMPLE 5
The Toxicity of Suramin and the Phosphonic Acid Agents in vivo in Mice A limitation on the clinical use of suramin is the narrow margin between the dose required to achieve anti-tumor activity and that leading to the onset of prohibitive toxic side effects. Suramin toxicity has been reviewed by LaRocca et al. (1990). It is clear that compounds with similar antitumor activity to suramin but with substantially lower toxicity would be of considerable potential therapeutic value as an antitumorigenic or antiangiogenic agent. Toxicity studies were performed with suramin, three sulfonic analogues more potent (2 times) than suramin in relation to inhibition of angiogenesis and endothelial cell growth and four phosphonic agents (10 to 40 times more potent). Mice were injected intraperitoneally with 0–150 $\mu$M/kg body weight of the compounds to be tested, every other day for a total of five injections. The animals were carefully observed daily and weighed every third day for 28 days after the last injection. After the 28-day observation period, the animals were euthanized, blood was collected through cardiac puncture and the following tissues were subjected to histological investigation: heart, lungs, liver, spleen, adrenal gland, kidney, sciatic nerve, soleus muscle and brain.

Animals treated with suramin at the highest dose (150 $\mu$M/kg body weight) died before completion of the five injections. We observed poor coat condition, weight loss, eye irritation and lacrimation by the end of the five injections in animals treated with suramin. The poor coat condition and reduction of 10–15% in body weight occurred at 150, 75 and 35 $\mu$M/kg body weight during the injection period. The coats and eye irritation became better but not normal and the body weight stabilized but did not return to normal over the subsequent 28 days of observation. A similar response was seen in two of the three sulfonic acid analogues that were tested. On the other hand, no mice treated with the four phosphonic acid agents died during the acute injection phase. Furthermore, their body weight did not decrease but they continued to gain weight at the same rate as the control animals at all levels of treatment. The body coat was normal and no eye irritation was noted in all animals treated with phosphonic acid agents.

Histological analysis of the tissues from animals treated with suramin showed a dose-related frequency of lipoid degeneration of the zona reticularis of the adrenal gland and vacuolar changes in the proximal convoluted tubules of the renal tubular epithelium. The animals treated with equimolar doses of the phosphonic analogues showed no significant changes in any important pathologic microscopic findings in those tissue samples.

These studies clearly indicate that the phosphonic acid agents show significantly lower toxicity than suramin and its trisulfonic acid analogs.

EXAMPLE 6
Structure-activity Relationship for the Antiangiogenic Activity of the Phosphonic Acid Agents Growing Vessels in the Chick Chorioallantoic Membrane Assay The phosphonic acid agents are extremely potent antiangiogenic compounds with molecular weights that are about half that of suramin. The phosphonic acid agents are up to 30 times more active than suramin in the CAM assay. Furthermore, the nonspecific binding of these compounds to serum proteins is lower than suramin and probably, as a consequence, a higher proportion is available in the free form to the cells and the half life is shorter. The size of the molecule also appeared important. Ten of the phosphonic acid agents have molecular weights of less than 600 and contained small central urea bridges (see Table 1), showed less antiangiogenic activity than the seven phosphonic acid agents which have big central urea bridges and higher molecular weights (650–900) (see Table 2). A third group of four phosphonic acid agents with miscellaneous structures is shown in Table 3.

There is considerable variation in antiangiogenic activity in compounds of similar structure. For example, NF 068, which is structurally very similar to NF 067, NF 069 and NF 681 (all are phosphonic acid agents with the same molecular weight), showed a substantial difference in the antiangiogenic activity (0% inhibition) in comparison with the same concentration of NF 069 and NF 681 (90% inhibition). This suggests that slight steric modifications in the molecule can induce dramatic changes in the potency of inhibition of angiogenesis, opening new avenues for antiangiogenic drugs design.

EXAMPLE 7
The Structure Activity Relationship for Inhibition of bFGF Induced Cell Growth in Human Microvascular Endothelial Cells Dose response curves were determined for the most active agents in human microvascular endothelial cell cultures treated with various concentrations in the presence or absence of bFGF. Inhibition of cell growth was evaluated by measuring total protein and total DNA and the IC50 was estimated for each dose response curve. The most potent compounds in relation to the inhibition of bFGF-induced endothelial cell growth were the phosphonic acid agents.

Our results show a close correlation between the inhibition of angiogenesis in vivo and the inhibition of endothelial cell stimulated growth in culture for the selected agents.

Among the five most active agents in vitro, four were phosphonic acid agents, the same compounds which were the most antiangiogenic in the CAM assay. These results suggest that the inhibition of angiogenesis in vivo in the CAM assay may involve a specific suppression of endothelial cell growth. Thus, we have identified a specific group of phosphonic acid agents with significantly lower molecular weight, less charged and much higher antiangiogenic activity than suramin and its sulfonic acid analogs.

The finding that a unique chemical group of the phosphonic acid agents, are much more potent as antiangiogenic compounds, less toxic and with shorter half-lifes than suramin, suggest that the phosphonic acid agents are of clinical significance and widen the therapeutic window for treatment of angiogenic dependent diseases.

EXAMPLE 8
Differences in the Inhibitory Effects of Suramin and the Phosphonic Acid Agents to bFGF-stimulated and Non-stimulated Endothelial Cells Suramin is a highly charged molecule with six sulfonate groups that are ionized at physiologic pH. This results in significant nonspecific binding to polypeptide growth factors (Coffey et al., 1987). However, suramin also exhibits a degree of specificity by binding to specific sites on a growth factor, similar to heparin binding to bFGF (Middaugh et al., 1992). While these studies showed that suramin is able to disrupt the binding of growth factors to their receptors in intact cells, it has diverse effects on other key enzymes involved in signal transduction and mitogenesis that probably contribute to its antiproliferative and antimetastatic activities. Our data showed that bFGF induced a dose-related increase in total protein and total DNA in human dermal microvascular and porcine pulmonary artery endothelial cells.

The presence of suramin (210 $\mu$M) inhibited the growth factor stimulatory effect, as has also been reported by Takano et al. (1992) and Braddock et al. (1994) for bovine aorta and bovine adrenal microvascular endothelial cells. In the presence of much lower concentrations (25 $\mu$M), the phosphonic agents, NF 067, NF 069 and NF 681, not only inhibited the stimulation of endothelial cell growth by bFGF but significantly reduced total protein content far below the unstimulated control endothelial cells.

These results show that the phosphonic acid agents are much more potent than suramin in inhibiting angiogenesis and that mechanisms other than blocking growth factor binding to endothelial cells play a very important role in their antiangiogenic activity. Results with suramin are similar to those reported in the literature (Takano et al., 1992 and Braddock et al., 1994) that suramin inhibited bFGF binding in a dose-related manner; but the phosphonic analogues in the same molar concentrations used for suramin did not affect either the total or the specific binding of the iodinated growth factor to the endothelial cells.

The percentage of inhibition of $I^{125}$ bFGF binding to low and high affinity binding sites of human microvascular endothelial cells was 96% at 70 $\mu$M of suramin, decreasing to 9% at 25 $\mu$M of suramin. However, for the same concentrations of phosphonic acid agents, the inhibition of growth factor binding was always less than 5% in relation to the control. These data clearly show that there is identified a chemical group of phosphonic acid agents that are very potent as antiangiogenic agents that express their activity through different mechanisms than those widely accepted for suramin.

The phosphonic acid agents are very inhibitory in the actively growing vessels of the 6-day CAM but showed almost no activity on the established vessels of the 11-day CAM. When compared with the MTT assay confluent and low density cultures in log phase growth, the phosphonic acid agents are 10-fold more inhibitory for growing cultures than for confluent human microvascular endothelial cell cultures. This in vitro finding corroborates our data with the CAM assay in different phases of growth, suggesting that this new class of suramin analogues target growing blood vessels and does not effect established blood vessels.

EXAMPLE 9
Differences in the Growth Inhibitory Effects of Suramin and the Phosphonic Acid Analogues in Human Microvascular Endothelial Cells and Established Cancer Cell Lines in Culture We have compared the activity of suramin and the phosphonic acid agents on some tumor cell lines proliferation in vitro and compared this activity with the antiangiogenic activity of these compounds in the CAM assay and their inhibitory activity in human microvascular endothelial cell growth. The MTT assay (Carmichael et al., 1987) was used to examine the effects of suramin and selected phosphonic acid analogues on cell proliferation. Suramin and the phosphonic acid agents inhibited cell proliferation in a dose-related manner. Analysis of the inhibitory action of suramin and the phosphonic acid agents in adrenal cortex carcinoma (SW13), human pancreatic adenocarcinoma (CFPAK-1), human prostate carcinomas (LNCap and PC3) showed IC50 value equipotent or less than suramin. In other cell lines, such as human breast carcinomas (MCF7 and T47D), human fibrosarcoma (HT1080), human colon adenocarcinoma (CaCo2), human glioblastoma (U87), kidney carcinoma (A498) and lung carcinoma (A427), the phosphonic acid agents showed equipotent or lower inhibitory activity in comparison to suramin.

Our data strengthened our important finding that the phosphonic acid agents are much more potent inhibitors of angiogenesis in the CAM assay and to human microvascular endothelial cell growth than suramin. This effect is not observed with some cancer cell lines. This suggests that there is specificity for endothelial cells in the antiangiogenic effect of the phosphonic acid agents.

EXAMPLE 10
Comparative Toxicity of Suramin, Trisulfonic Analogues and the Phosphonic Acid Agents in vivo in Mice A limitation on the clinical use of suramin is the narrow margin between the dose required to achieve anti-tumor activity and that leading to the onset of prohibitive toxic side effects. Suramin toxicity has been reviewed by LaRocca et al. (1990). It is clear from studies so far that compounds with equipotent or greater antitumor activity but with substantially lower toxicity are of considerable potential therapeutic value as an antitumorigenic or antiangiogenic agent. Preliminary toxicity studies were performed with suramin, three sulfonic analogues more potent (2 times) than suramin in relation to inhibition of angiogenesis and endothelial cell growth and the four most active phosphonic analogues (up to 30 times). Mice were injected intraperitoneally with suramin or equimolar doses of the sulfonated analogues or the phosphonic analogues or the phosphonic acid agents (1–150 $\mu$M/Kg body weight) every other day for a total of five injections. The animals were carefully observed daily and weighed every third day for 28 days after the last injection. After the 28-day observation period, the animals were euthanized, blood was collected through cardiac puncture and the following tissues were kept for histological investigation: heart, lungs, liver, spleen, adrenal gland, kidney, sciatic nerve, soleus muscle and brain.

Animals treated with suramin at the highest dose (150 $\mu$M/Kg body weight) died before completion of the five injections. Poor coat condition, weight loss, eye irritation and lacrimation was observed by the end of the five injections in animals treated with suramin. The poor coat condition and reduction of 10–15% in body weight occurred at 150, 75 and 35 $\mu$M/Kg body weight during the injection period. The coat condition and eye irritation became better but not normal and the body weight stabilized but did not return to normal over the subsequent 28 days of observation. On the other hand, mice treated with the phosphonic acid agents did not die during the acute injection phase. Furthermore, their body weight did not decrease but they continued to gain weight at the same rate as the control animals at all levels of treatment. The body coat was normal and no eye irritation was noted.

Histological analysis of the tissues from animals treated with suramin showed a dose-related frequency of lipoid degeneration of the zona reticularis of the adrenal gland and vacuolar changes in the proximal convoluted tubules of the renal tubular epithelium. The animals treated with equimolar doses of the phosphonic acid agents showed no significant changes in any important pathologic microscopic findings in those tissue samples. These preliminary studies clearly indicate that the phosphonic acid agents show a greater than 10-fold increase in antiangiogenic activity and significantly lower toxicity.

EXAMPLE 11
Structure of Phosphonic Acid Agents

The phosphonic acid agents studied were selected based on the criteria of drug potency in relation to inhibition of angiogenesis in the CAM and inhibition of microvascular endothelial cell growth in vitro, availability, chemical purity and sampling of each different chemical structure subgroup. Twenty-two phosphonic acid agents, including NF 067, NF 068 NF 069, NF 681, and NF 162, synthesized by our laboratory, are used in various concentrations. In the CAM assay, the ID50 for suramin was 75 nmol and the ID50 for the phosphonic acid agents, NF 069, NF 681 and NF 067, was respectively, 9, 2 and 32 nmol. The estimated IC50 for suramin in the bFGF-stimulated human microvascular endothelial cells was 437 $\mu$M and for NF 069, NF 681 and NF 067 were respectively, 75, 1.5 and 19.4 $\mu$M, reflecting activity that is up to 200 times more potent than suramin. NF 068 is a closely related compound chemically which does not show any antiangiogenic activity. The structures of these phosphonic acid agents and suramin are shown in Tables 1–3.

The inventors have identified a clear correlation between the chemical structure and antiangiogenic activity. The phosphonic acid agents are far more potent inhibitors of angiogenesis and bFGF-stimulated endothelial cell growth than any suramin. Furthermore, the phosphonic acid analogues with large central urea bridges are in general more active than the group with small central bridges or other configurations.

EXAMPLE 12
Effects of the Phosphonic Acid Agents and Suramin on DNA Synthesis and Human Microvascular Endothelial Cell Growth $^3$H-Thymidine incorporation is used to determine the effect of the phosphonic acid agents and suramin on DNA synthesis in HMEC-1 and HMVEC-d cells. Logarithmically growing HMEC-1 or HMVEC-d cells are seeded at $2\times10^4$ cells/well in six well plates (Falcon) containing 2 ml of MCDB-131 medium supplemented with 5% fetal bovine serum (FBS) (Hyclone). Various amounts of suramin (0–500 $\mu$M) and equimolar concentrations of the phosphonic acid agents are added to different wells, and the plates incubated for 24 hr. $^3$H-Thymidine (ICN Radiochemicals) is added and incorporation allowed to proceed for an additional 30 min. After removal of medium, the cell layer is washed twice with 1 ml of cold Hanks balanced salt solution and the cells are dislodged by trypsinization. The cells are collected in microcentrifuge tubes and washed twice with 1 ml of cold phosphate-buffered saline, and then 1 ml of cold 10% trichloroacetic acid are added. Acid precipitable radioactivity are collected on a glass fiber filter (Whatman Grade GF/C) and the radioactivity is determined in a liquid scintillation spectrometer (Packard).

The effect of various concentrations of suramin and the phosphonic acid agents on cell growth and ongoing DNA synthesis is measured. The inventors found that concentrations of suramin up to 100 $\mu$g/ml did not have any significant inhibitory effect on HMEC-1 and porcine pulmonary artery macrovascular endothelial cell growth. As a matter of fact, a stimulatory effect on cell growth with suramin at 50–100 $\mu$g/ml was detected. However, at concentrations higher than 250 $\mu$g/ml, there was a significant dose-related reduction in total protein and total DNA. The phosphonic acid agents always showed potent reduction in total protein and total DNA even at lower concentrations, suggesting, once again, a different and specific mode of action on endothelial cells by the agents.

EXAMPLE 13
The Time Course for Inhibition of Protein Synthesis by the Phosphonic Acid Agents in Human Microvascular Endothelial Cells $^3$H-Leucine incorporation is used to determine the effect of the phosphonic acid agents and suramin on protein synthesis in HMEC-1 and HMVEC-d cells. HMEC-1 or HMVEC-d cells are grown to confluence in flasks (P100) and IC50 doses of the phosphonic analogues or suramin are added for time periods of 6 to 36 hr. For each time period, six replicate flasks are set up. The volume of the medium MCDB-131 is 10 ml per flask. After incubation, the medium was replaced with fresh MCDB-131 containing 0.37 MB ml of $^3$H-leucine and incubated for a further 90 min. TritonX-100 (240 $\mu$l, 10%) were then added to the contents of each flask and agitated. Trichloroacetic acid (TCA) (4 ml, 20%) is added, the contents mixed and the flasks left overnight at room temperature. After 24 hr, the flask contents was suspended by shaking, transferred to tubes and centrifuged at 4300 g. The pellets were resuspended in 10% TCA and recentrifuged and then resuspended in 3.0 ml of 0.1 M NaOH. Half of this volume was transferred to scintillation vials in 10 ml of Emulsifier Safe scintillation fluid (Packard) while the remaining 1.5 ml was used to assay DNA content (LaBarca and Paigen, 1980). The radioactive counts due to protein synthesized in the presence of $^3$H-leucine was normalized to counts/$\mu$g DNA. Protein synthesis by cells treated with the phosphonic acid agents are expressed relative to that of control cells as the percent of inhibition for each time of incubation.

Comparison of $^3$H-leucine incorporation into cellular protein in the presence or absence of suramin and the phosphonic acid agents was used as a measure of the inhibition of protein synthesis. There was no change in the rate of protein synthesis until suramin and the cells have been incubated together for at least 24 hr. It was shown that this is the time necessary for a reasonable amount of suramin to be taken up by HMEC-1 cells (Gagliardi et al., 1996). After this period of time, the rate steadily declines. The inhibition of protein synthesis by the phosphonic acid agents was significant after a short time of incubation because these compounds are smaller and less charged than suramin.

EXAMPLE 14
Determination of the Sensitive Phase of the Cell Cycle for the Inhibitory Effects of the Phosphonic Acid Agents and Suramin on Human Microvascular Endothelial Cells Suramin has been shown to inhibit cell cycle progression at different phases in various cancer cell lines. There is no data available on the effect of the phosphonic acid agents and suramin on cell cycle in human microvascular endothelial cells. Jindal et al. (1990) first described the inhibitory action of suramin on DNA synthesis and proposed that it was due to a direct action on cellular DNA polymerases. Data from in vitro studies suggest that the optimal benefit from suramin may require prolonged exposure time. It has been reported that prostate carcinoma cells, treated in vitro with suramin, are slowly arrested in the G1 phase. Cell arrest in the G1 phase became evident only after 24 hr of exposure and suramin also induced a decrease in cells in the S phase (Qiao et al., 1994). Suramin inhibited proliferation of human cerebral meningioma cells and increased the percentage of cells in the S and G2/M phase of the cell cycle. As suramin simultaneously decreased the proliferation rate shown by direct cell counting and $^3$H-thymidine uptake, the effect in the G2/M phase cannot be attributed to increased proliferative activity.

Consequently, suramin must lead to a prolongation of the S and G2/M phases or to an arrest during these cell cycle phases. However, the data showed that the human microvascular endothelial cells are much more sensitive to inhibition by both suramin and the phosphonic acid agents than the large vessel endothelium, suggesting a stronger promoting activity of bFGF on microvascular as opposed to macrovascular endothelial cells, as described by Braddock et al. (1994).

EXAMPLE 15

Effects of the Phosphonic Acid Agents on the Transit Time of Endothelial Cells Through the Cell Cycle Experiments using flow cytometry are performed to determine the effects of the phosphonic acid agents at different doses and comparing them to the results with suramin. HMEC-1 and HMVEC-d synchronized cells are used to analyze the effects of selected phosphonic acid agents on the distribution of cells in the various phases of the cell cycle using the propidium iodide method according to Vindelov et al. (1985). Briefly, $10^4$ cells are seeded with MCDB-131. After 24 hr, the medium is replaced with fresh medium containing the test compounds at 0–500 $\mu$M. After exposure times of 12, 24, 48 and 72 hr, the cells are collected by trypsinization, stained with propidium iodide and analyzed by flow cytometry for the percentage of cells in G0/G1, S, and G2/M phase.

These studies compare the effects of the phosphonic acid agents on the percentage of cells in different phases of the cycle for human microvascular endothelial cells. These results enable us to understand if the same mechanisms are involved in the inhibition of endothelial cell growth by phosphonic acid agents and suramin.

EXAMPLE 16

Determination of the Involvement of Cell Signaling Pathway Components, Protein Kinase C and p34CDC2 Kinase, on the Inhibition of Human Microvascular Endothelial Cell Growth by the Phosphonic Acid Agents Many studies have unraveled the importance of cell signaling pathways in the inhibitory action of certain compounds. Protein kinase C (PKC) is involved in apoptosis induction by some compounds, and suramin has been shown to inhibit PKC. Suramin inhibits PKC type I–III activity in a concentration-dependent manner with an ID50=50 $\mu$M. The inhibition of cyclic AMP-dependent protein kinase activity was much less sensitive to suramin with an IC50= 656 $\mu$M (Mahoney et al., 1990). Similar inhibitory effects were observed with M-kinase, the constitutively active catalytic fragment of PKC, and autophosphorylation of PKC types I–III.

PKC consists of a family of gene products in animal tissues composed of at least ten distinct proteins (alpha, beta, gamma, delta, epsilon, eta, theta, zeta, iota and mu) that are important regulatory elements in signal transduction, cellular regulation and tumor promotion. It has been shown that endothelial cell proliferation in response to bFGF is dependent upon activation of PKC (Kent et al., 1995) and that activation of PKC is both necessary and sufficient for attachment, spreading and migration of human endothelial cells (Yamamura et al., 1996). The distribution of PKC isotypes is cell specific. The discovery of these isotypes that have distinct physiologic functions provides an explanation for the plethora of cellular events that are mediated by PKC. Investigation of PKC isotypes in human umbilical vein macrovascular endothelial cell (HUVEC) with Northern and Western blot analyses demonstrated the presence of PKC alpha, delta, epsilon, eta, theta and zeta (Haller et al., 1996). Endothelial cell stimulation by bFGF has been well documented to increase cytosolic and perinuclear PKC alpha and epsilon immunoreactivity. These same PKC isotypes were markedly down regulated after prolonged treatment with phorbol esters (Yamamura et al., 1996).

The down regulation of PKC alpha and epsilon inhibited endothelial cell migration and proliferation. These findings suggest that PKC alpha and epsilon are the isotypes involved with cytoskeleton events, endothelial cell migration and the proliferative response to bFGF. Because of the importance of PKC in regulating pleiotropic biological processes, it is of importance to identify the inhibition of PKC by the phosphonic analogues in endothelial cells.

EXAMPLE 17

Effects of the Phosphonic Acid Agents on PKC Activity, in situ, in Human Microvascular Endothelial Cells in Culture HMEC-1 or HMVEC-d cultures are grown to confluence on gelatinized 96-well plates. After a 24-hr incubation with the MCDB-131 culture medium containing 5% FBS, cells are washed with MCDB-131 only and then incubated with the experimental media. Several experiments are necessary to understand the role of the phosphonic acid agents on PKC. Confluent cells are treated with bFGF (10 ng/ml) in the presence or absence of suramin (100, 200, 400 and 800 $\mu$g/ml) or equimolar concentrations of the phosphonic acid agents for 5–10–30–60 and 120 minutes. Confluent cultures are treated with the active phorbol esters, PMA and PDD (10–200 ng/ml), and the inactive analogue, 4-$\alpha$-PDD (Montesano and Orci, 1985) in the presence or absence of suramin or selected phosphonic acid analogues. A specific inhibitor for PKC, RO-318220, is also used in a similar manner as the control. After the indicated time points, the cells are washed with cold PBS and PKC is assayed with (Ac-MBP(4-14)), which acts as specific substrate of PKC (Koide et al., 1992). To each well, 100 $\mu$l total volume of the following are added: lysis buffer (final concentration: 0.137 mM NaCl, 5.4 $\mu$M KCl, 0.3 $\mu$M Na$_3$PO$_4$, 0.4 $\mu$M K$_2$HPO$_4$, 1 mg/ml glucose, 20 miM HEPES, 10 mM MgCl$_2$, 50 $\mu$g/ml digitonin and 25 mM B-glycerophosphate, pH 7.2), 100 $\mu$M (gamma32P) ATP, 2.3 mM CaCl$_2$, 2$\mu$g/ml phosphatidylserine, and 100 $\mu$M Ac-MBP. After incubation, 50 $\mu$l from each well are spotted onto phosphocellulose disks, washed with 1% concentrated H$_3$PO$_4$ in water, and counted. Results are expressed as the percentage of inhibition in comparison to cultures treated with bFGF or active phorbol esters.

The phosphonic acid agents show a strong inhibitory effect on PKC activity and this effect can be counter balanced by the addition of active phorbol esters. A clear inhibition of PKCà, the isotype that seems to play the most important role in endothelial cells.

EXAMPLE 18

PKC Isotypes Involved in Induction of Apoptosis in Microvascular Endothelial Cells Several experiments are necessary to understand which isotypes of PKC respond to cell growth and apoptosis. The expression of different PKC isotypes are determined in subconfluent cultures, confluent quiescent cultures, subconfluent cultures treated with bFGF or VEGF, subconfluent cultures treated with each of the phosphonic acid agents and subconfluent cultures treated with bFGF or VEGF. Subconfluent cultures are also treated with the active phorbol esters (10–200 ng/ml), PMA and PDD and the inactive analog, 4 à-PDD (control) (Montesano and Orci, 1985). HMEC-1 and HMVEC-d cells are also treated with the phorbol esters in the presence or absence of the various phosphonic acid analogues. A specific inhibitor for PKC, RO-318220, are also used in a similar manner with and without the phosphonic acid analogues (Tsopanoglou, 1994).

The total RNA is extracted and the mRNA for the specific isotypes is determined by Northern blots as described by Mattila et al. (1994). The protein for each specific PKC isotype is separated and determined by Western blot analysis (Mattila et al., 1994). The measure of apoptosis is carried out in dishes treated in the same fashion as described above. Cells are analyzed for apoptosis as described.

The conventional PKC isotypes (alpha, beta, gamma) are calcium and phospholipid dependent whereas the novel isotypes (delta, epsilon, eta and theta) do not require calcium for activation. Zeta is both calcium and phorbol ester independent. The isotypes have not been reported in any human microvascular endothelial cells. However, for the rat macrovascular and human macrovascular cells, only alpha and epsilon appear to be involved in growth. The experiments show which PKC isotypes are stimulated by phorbol esters or are inhibited by the phosphonic acid analogues. A major goal is to determine if these PKC isotypes can overcome their inhibition by phosphonic acid analogues when treated with phorbol esters. This would suggest that PKC is a major pathway for the induction of apoptosis in the human microvascular endothelial cells.

EXAMPLE 19
Effects of the Phosphonic Acid Agents on p34CDC2 Kinase Activity in Human Microvascular Endothelial Cells in Culture CDC2 kinase is the key enzyme controlling G2-M transition in human cells and its inactivation results in cell cycle interruption and G2 block (Bojanowski et al., 1994). In studies using DNA flow cytometry, suramin inhibited meningioma cell proliferation in five different tumor lines by arresting cells in G2-M and S phases of the cell cycle (Schrell et al., 1995). These effects were found under serum-containing and serum-free culture conditions, and in the absence or presence of estradiol or insulin-like growth factor-1. Prolonged exposure (48 hr) to suramin caused an accumulation of MCF-7 human breast cancer cells in the G2-M phase of the cell cycle (Foekens et al., 1993). Suramin has a direct inhibitory effect on purified cdc2 kinase and also modulates the tyrosine phosphorylation of cdc2 kinase in extracts from human small cell lung cancer cells, suggesting that suramin might have a double inhibitory effect on cdc2 kinase in vivo: one blocking the kinase activity and the second, protecting the tyrosine phosphorylation of the enzyme. CDC kinase was found to be important in cell proliferation, and suramin was reported to influence this kinase as well.

The effects of selected phosphonic acid agents on the p34cdc2-related kinase activity are carried out essentially as described by Bojanowski et al. (1994).

Cytoplasmic and nuclear extractions: 100 million cells (HMVEC-1 or HMEC-d) are washed twice with cold PBS and incubated in hypotonic phosphate buffer for 45 min on ice. The cells are then disrupted with a Dounce homogenizer and nuclei separated from the cytoplasmic fraction by centrifugation and extensive washing with hypotonic buffer. The nuclei are incubated for 30 min in the presence of 350 mM NaCl and the nonsoluble nuclear material removed by ultracentrifugation (20 min at 40000 rpm in TL 100 Beckman ultracentrifuge). The protein concentration are adjusted to 1.5 mg/ml, 20% of glycerol are added and the extracts stored at −20° C.

p13-agarose precipitation: extracts (300 µg protein) or purified p34cdc2 kinase (50 ng protein) are diluted in 400 µl of precipitation buffer in the presence and absence of suramin (0–20–120 µM) or the phosphonic acid agents in equimolar concentrations. After 10 min, 15 µl of p13-agarose are added and samples incubated at 4° C. for 1–3 hr. The samples are subjected to a brief centrifugation, the supernatant eliminated and the precipitates are washed four times in precipitation buffer with vortexing and transferred to a clean Eppendorf tube after the third wash. The precipitates are used immediately for kinase assays or Western blot.

p34cdc2 kinase assay: 25 ng of purified p34cdc2 kinase or p-13 agarose precipitates are incubated in 20 µl of kinase buffer, 32P-ATP and p34cdc2 kinase substrate, with or without suramin and the phosphonic acid agents at 25° C. for 20 min. Reactions are stopped by placing the samples on ice and spotting 5 µl of the reaction mixture onto P81 phosphocellulose filters (Whatman). Filters are washed three times in 50 mM phosphoric acid, dried and the radioactivity retained on the filters are determined by liquid scintillation (Beckman).

Western blot: the precipitates are electrophoresed in 12.5% 12×12 cm ready-made polyacrylamide gels (Daichi Co.) and the proteins transferred to Immobilon PVDF membranes (Millipore). Nonspecific binding sites on the membranes are saturated with 5% skim milk in PBS. The immobilized antigens are revealed using bitinylated secondary antibodies with biotinyl-tyramide/streptavidin reagent (Blast kit, Dupont, USA) to increase the sensitivity of the signal and Nitrotetrazolium/NADH substrate (POD kit, WAKO, Japan) to visualize it. A Pharmacia LKB image master DTS chromoscan are used for band quantification (Bojanowski et al., 1994).

Suramin inhibits p34cdc2 kinase activity in a dose-related manner and the phosphonic acid agents are also potent p34cdc2 kinase inhibitors. Suramin has been reported to increase the global tyrosine specific phosphorylation of cellular proteins in vivo and the first suramin-sensitive tyrosine phosphatase has recently been described (Ghosh and Miller, 1993). The Western blot shows different electrophoretic mobility p34cdc2 kinase bands between samples treated or not treated with suramin and the phosphonic acid agents, and the immunoblot with anti-phosphotyrosine antibody exhibits a difference in p34cdc2 kinase tyrosine phosphorylation.

EXAMPLE 20
Programmed Cell Death (Apoptosis) Induced by Phosphonic Acid Agents in Human Microvascular Endothelial Cells To measure the induction of apoptosis by the phosphonic acid agents, quiescent and exponentially growing endothelial cells are analyzed. After 24 hr of seeding (low cell density) or after confluence is reached (high cell density), the medium is changed with fresh medium containing various amounts of the phosphonic acid agents. The experiments with confluent cultures are carried out also in the presence or absence of bFGF (10 ng/ml). After various exposure times (6–36 hr), the cells are harvested and analyzed for the induction of apoptosis by four different methods:

a) The cells are fixed with 70% ethanol, spread onto microscope slides, stained with acridine orange and analyzed for nuclei (500 cells counted per data point).

b) The cells are fixed in 4% buffered formalin, air dried onto lysine coated slides, quenched for endogenous peroxidases with 2% hydrogen peroxide, treated with terminal deoxyribonucleotide triphosphatase, followed by anti-dioxigenin-peroxidase, DAB substrate solution and finally, methyl green. Cells (100) are counted to determine the percentage of Apotag-positive cells per data point.

c) To demonstrate DNA fragmentation (DNA laddering), harvested cells are treated with protease k and sodium dodecyl sulfate for 12 hr to degrade cellular protein. The DNA are extracted with phenol/chloroform/isoamyl alcohol, followed by ethanol precipitation. The air dried DNA pellet is re-suspended in TE buffer and run on a 1% agarose gel for 2 hr at 120 volts. The gels are stained with ethidium bromide and photographed.

d) To determine the time course of events more exactly and to discover whether the cells enter apoptosis from the G0/G1 stage or S/M stages, a new flow cytometry method established in our Flow Cytometry Core Facility based on the method of Reid et al. (1996) is used. The harvested cells are stained with Hoechst 33342 and merocyanine 540, analyzed by flow cytometry and divided in five groups: viable G0/G1, viable s/G2/M, early apoptotic G0/G1, early apoptotic S/G2/M, and fragmented DNA (late apoptotic) cells.

The phosphonic acid agents induce programmed cell death in human microvascular endothelial cells that are actively proliferating and that the apoptosis process is triggered by cell detachment.

EXAMPLE 21
Uptake and Intracellular Distribution of $^3$H-phosphonic Acid Analogues by Human Microvascular Endothelial Cells We have already shown that $^3$H-suramin is taken up by human microvascular endothelial cells in culture and that suramin is probably transported by the caveolae system. The suramin incorporation by HMEC-1 cells increased and reached a plateau around 24 hr of incubation, and more than 50% of the suramin taken up by HMEC-1 cells went to the nucleus. Our group is synthesizing various tritiated phosphonic acid agents that are used for experiments in HMEC-1 and HMVEC-d cells. Briefly, tritiated suramin (13 $\mu$Ci/100 ml of MCDB-131 without FBS) obtained from Moravek Biochemicals (Brea, Calif.) was incubated at 37° C. in 5% $CO_2$/air for different periods of time (2–72 hr). Triplicates were carried out for each period of incubation. At the end of each incubation period, the cells were processed through different washings and finally to differential centrifugation. Different cell fractions were transferred to separate scintillation vials, solubilized in a liquid scintillation cocktail and counted in a 2000 CA TRICARB Liquid Scintillation Counter.

The phosphonic acid analogues are taken up by HMEC-1 and HMVEC-d cells much faster and in higher amounts than suramin because the phosphonic acid agents are smaller, less charged molecules than suramin and less bound to proteins. The demonstration that the phosphonic acid agents can reach significant intracellular concentrations and its localization is very important for the understanding of the mechanism of action of these compounds.

EXAMPLE 22
Effects of Phosphonic Acid Agents on Programmed Cell Death in the Chick Chorioallantoic Membrane (CAM)

The CAM assay has been reported as a suitable model for the demonstration of "in vivo" induced apoptosis (Brooks et al., 1994). We have shown that suramin and the phosphonic acid agents are potent inhibitors of angiogenesis in the 6-day CAM assay. To explore the possibility that suramin and/or the phosphonic acid agents induce apoptosis in vascular cells, 6-day old chick embryos are treated with suramin or the phosphonic acid agents (0–200 $\mu$M) and injected in the CAM fluid (in the 6-day CAM, the angiogenic vessels grow rapidly embedded with CAM fluid). After 24, 48 and 72 hr of treatment with the compounds or saline as control, the CAMs are resected for DNA isolation and analysis for oligonucleosomal fragmentation as previously described by Brooks et al., (1994). To identify those cells within the CAM undergoing apoptosis in response to the treatment with the phosphonic acid agents, cryostat sections prepared from CAMs treated for 24–48 and 72 hr are examined for apoptosis by the Apo-Tag immunoreactivity kit and for endothelial cell specific staining. Co-localization of these markers in the same cells demonstrate that inhibition of angiogenesis by the phosphonic acid agents in vivo in the 6-day CAM assay involves induction of programmed cell death of microvascular endothelial cells.

EXAMPLE 23
Inhibition Effects of Phosphonic Acid Agents on Integrins and Human Microvascular Endothelial Cell Adhesion The adhesion receptor integrin, $\alpha v\beta 3$, has recently been identified as a marker of angiogenic blood vessels in the chick chorioallantoic membrane and in humans (Brooks et al. 1994). It was also apparent that this integrin played a very important role in angiogenesis. Topical application of a specific antibody against $\alpha v\beta 3$ prevented the growth of new blood vessels in the chick CAM in response to cytokines and fragments of tumors (Brooks et al., 1994). In vitro, cell interaction with extracellular matrix has been shown to be related to induction of cell proliferation, motility, gene expression and programmed cell death (Ruoslahti and Reed, 1994; Meredith et al., 1993). In fact, recent studies have shown that ligation of $\alpha v\beta 3$ on human endothelial cells in vitro promotes a rise in calcium and pH (Leavesley et al., 1993), activation of focal adhesion kinase (Defillipi et al., 1994) and the polymerization of the actin cytoskeleton (Sastry and Horwitz, 1993), which in turn regulates cellular shape and motility of endothelial cells on the extracellular matrix. These signaling events triggered by integrins probably play an important role in the functions and survival of microvascular endothelial cells undergoing angiogenesis.

It has been shown that prevention of ligation of the $\alpha v\beta 3$ integrin to the extracellular matrix promotes apoptosis of microvascular endothelial cells which have been induced by angiogenic growth factors to enter the cell cycle. After differentiation has occurred and mature blood vessels formed, integrin $\alpha v\beta 3$ signaling is no longer required for survival of the microvascular endothelial cells and they become refractory to the deleterious effects of the specific integrin antagonists. In conclusion, antagonists of integrin $\alpha v\beta 3$ disrupt newly forming blood vessels without affecting the preexisting vasculature (Brooks et al., 1994).

We observed that cultures of human microvascular endothelial cells treated with suramin and more clearly with the phosphonic acid agents showed a large number of floating cells after 24 hr of treatment. Similar findings were reported by Pepper et al. (1994) with bovine microvascular endothelial cells treated with suramin, and by Mitchen et al. (1993) with primary epithelial cell cultures from human prostate treated with suramin. When endothelial cells are cultured under conditions that prevent adhesion and spreading, they stop growing, become detached, acquire a round cell shape and enter programmed cell death (Re et al., 1994).

The regulation of integrin function by the urokinase receptor has also been reported (Wei et al., 1996), suggesting that reagents that affect the urokinase receptor can alter integrin function by disrupting the urokinase plasminogen receptor-integrin association representing potential therapeutic agents for tumor invasion and progression. The specific inhibition of the activity of the urokinase receptor mediated cell surface plasminogen activation system by suramin and the direct effect of suramin on the cell surface associated with the urokinase receptor has already been shown (Behrendt et al., 1993; Ellis and Dano, 1993; Pepper et al., 1994). We postulate that the phosphonic acid agents might interfere with microvascular endothelial cell adhesion to the extracellular matrix, altering integrin functions, causing endothelial cell detachment and consequential induction of apoptosis.

Cell attachment assay: The effects of the phosphonic acid agents in variable amounts (0–200 $\mu$M) on the interaction of human microvascular endothelial cells with components of the extracellular matrix, such as laminin (interacts with integrin $\alpha 2\beta 1$), fibronectin (interacts with integrin $\alpha 5\beta 1$) and vitronectin (interacts with integrin $\alpha v\beta 3$), are studied as described by Sriramarao et al. (1993). Briefly, different concentrations of the proteins (0–10 $\mu$g/ml) diluted in PBS are immobilized on 96 well plates by incubating overnight at 4° C. The unbound sites are then blocked with serum free medium (MCDB-131 containing 1% BSA and 10 mM HEPES) by incubating the wells for 1 hr at 37° C. The human microvascular endothelial cells are harvested after washing with PBS and incubating the cells with a PBS-based free enzyme free cell dissociation solution for 30 min at 37° C. The cell suspension are washed with free serum medium and resuspended at $5\times10^4$ cells/ml and 100 $\mu$l are added to each well. The plates are incubated for 1 hr at 37° C. For the anti-integrin antibody (used as positive control), the cells are preincubated for 30 min before being added to the protein coated wells. Plates are washed twice with PBS containing 1 mM calcium and magnesium to remove unbound cells. The adherent cells are fixed with 3.5% paraformaldehyde containing 0.5% crystal violet. Endothelial cells are gently washed and adherent cells quantitated by measuring the absorbance at 595 nm on a microtiter plate reader.

Human microvascular endothelial cells treated with the active phosphonic acid agents show a decrease in the percentage of cells attached in relation to the controls. This effect is dose-related. Furthermore, we expect to see more significant changes when the plates are coated with vitronectin because its interaction with integrin $\alpha v\beta 3$ is inhibited by polyanions (Panetti et al., 1995). It takes longer than 12 hr for the detection of any suramin toxicity on endothelial cells even at concentrations higher than 200 $\mu$M. Hence, any effect observed in this short time incubation experiment can be interpreted as solely due to inhibition of cell attachment to the extracellular matrix by the phosphonic acid agents.

EXAMPLE 24
Effects of the Phosphonic Acid Agents on the Production of Protease by Human Microvascular Endothelial Cells in vitro A tightly controlled increase in extracellular proteolysis, restricted both in time and space, is a very important component of the angiogenic process. This has led to the notion that compounds capable of inhibiting proteolysis could be effective in inhibiting angiogenesis (Pepper et al., 1994). Indeed, protease inhibitors do inhibit angiogenesis and suramin has been shown to alter the proteolytic properties of bovine microvascular endothelial cells. Suramin has been shown to significantly inhibit plasminogen activator activity induced by bFGF in fetal bovine aortic endothelial cells at concentrations higher than 250 $\mu$g/ml (Takano et al., 1994). These methods were established in our laboratory and used to study the effect of tamoxifen (a partial antiestrogen) on proteolytic properties of human microvascular endothelial cells. These same methods are used to determine the effects of phosphonic acid agents.

Human microvascular endothelial cells (HMEC-1 and HMVEC-d) are plated in 96 well culture plates. After 24 hr, the medium are replaced with fresh MCDB-131 containing 5% FCS and varying amounts of the phosphonic acid agents. The experiment is carried out in the presence or absence of 10 ng/ml bFGF. After 18–24 hr of incubation at 37° C. with 5% $CO_2$/air, the cells are washed and lysed. Total protein is determined in the lysate and 1 $\mu$g of total protein is used to determine plasminogen activator (PA) activity with a chromogenic method (American Diagnostica, CT) and with a microplate reader. Human urokinase (Calbiochem, La Jolla, Calif.) is used to generate the standard curve of PA activity. Results are expressed as the percentage of control activity. Zymographic analysis of PA is performed according to the method of Granelli et al. (1983).

The phosphonic acid agents express inhibitory activity on the proteolytic properties in a dose-related manner.

EXAMPLE 25
Effect of the Phosphonic Acid Agents on Cell Matrix Matalloproteinases (MMPs) in the Endothelial Cells Matrix metalloproteinases are an important group of zinc enzymes responsible for the degradation of the extracellular matrix components, such as collagen and proteoglycans. Currently, 16 family members have been identified. MMP family member differ from each other structurally by the presence or absence of domains that contribute to activities such as substrate specificity, inhibitor binding, matrix binding and cell surface localization (Powell and Matrisian, 1996). To determine if the phosphonic acid agents were effective inhibitors of the MMP's of endothelial cells, cells were incubated in the presence of the different agents for 48 hours. Tissue samples were taken and subjected to zymography. Tissue samples were placed in glass homogenizers in a three fold weight/volume of lysis buffer consisting of 50 mM Tris-HCL, pH=7.4, with 200 mM sodium chloride and 0.1% Triton X-100. The samples were homogenized and centrifuged at 1500 g for 20 min. The supernatant was immediately analyzed by zymography. Protein content of each sample was determined by a modified Lowry method.

MMP enzyme activity was detected using polyacrylamide gel eltrophoresis zymography. SDS-polyacrylamide gel electrophoresis (PAGE) was performed using 8% acrylamide gels containing 0.1% gelatin. The volume of test samples loaded was 15 $\mu$l. Electrophoresis was run at 4° C. at a constant voltage (100 volts). After electrophoresis, gels were incubated in Triton X-100 (2.5%) for 30 minutes to eliminate SDS, prior to being incubated overnight in 50 mM Tris HCL, pH7.5, containing 10 mM $CaCl_2$ at 37° C. The gels were stained in 0.25% (W/v) Coomassie Brilliant Blue and destained in methanol:acetic acid:water (50:40:10). The clear zones in these gels indicates the presence of proteins with gelatinolytic activity. This method allows for identification of pro-metalloproteinases. Migration position of proteins and with standard molecular weight and supernatant from HT 1080 cells that express MMP-2 and MMP-9 were used as controls.

The results with human microvascular endothelial cells are as follows: NF 050, NF 162 and NF 681 are potent inhibitors of MMP-2 activity. bFGF increased MMP-2 activity in human microvacular endothelial cells and these phosphonic acid agents inhibited the increase in MMP-2 activity induced by bFGF. These results suggest that the MMP-2 in endothelial cells may be an important component in the angiogenesis process. This inhibition of MMP-2 by the phosphonic acid agents may be an important mechanism for the inhibition of angiogenesis.

EXAMPLE 26
Effect of the Phosphonic Acid Agents on Cell Matrix Metalloproteinases (MMP's) in Cancer Cells in vitro For a tumor cell to metastasize, it must break away from its neighbors and penetrate through the surrounding stoma and the basement membrane to enter the circulation. The extensive degradation of the extracellular matrix component in tumor cells depends on the secretion of a battery of metalloendopeptidases that digest a wide range of proteins of the extracellular matrix (Woessner, 1991).

Several recent reports have shown a correlation between MMP expression and tumor invasiveness in prostate cancer. Pajough et al. (1991) found that MMP-7 was increased in malignant compared to benign prostatic tissue but absent in the stroma. Boag and Young (1993) found increased levels of gelatinase A (MMP-2) in malignant prostate and metastatic tissue. Stearns and Wang (1993) analyzed prostrate cancer tissue extracts for gelatinase A (MMP-2) using Northern blot studies. Their results suggested that the enzyme is selectively overexpressed by malignant preinvasive epithelial cells with very low levels in benign tissue and the stroma surrounding the tumor. Wilson et al. (1993) reported gelatinolytic proteinase activities in human prostate secretions, with an increased level of expression in neoplastic compared to benign disease. The results presented by Hamdy et al. (1994) suggest that MMP-9 activity is increased in malignant compared to benign prostatic tissue. The gelatinase B (MMP-9) was not expressed in benign tissue but was detected in 42% of prostate carcinomas. Furthermore, those who exhibited MMP-9 activity in vitro had particularly unfavorable clinical parameters, including well-established prognostic factors, such as high Gleason scores, serum PSA levels and primary tumor ploidy. Furthermore, 100% of the patients that did not respond to treatment expressed MMP-9.

Metalloproteinases have long been associated with metastasis and are major functional contributors to the metastatic process. MMP's are important contributors to the initial growth of metastasis, regulating access to growth factors from the extracellular matrix and increasing angiogenesis (Chambers and Matrisian, 1997). Activated MMP's are susceptible to inhibition by the general serum proteinase inhibitor, α-2-macroglobulin, and by a family of specific tissue inhibitors of metalloproteinases (TIMP). The two major members of this family, TIMP-1 and TIMP-2, are expressed by a variety of cell types. They form non-covalent, stoichiometric complexes with both latent and active MMP. TIMP-1 is associated with progelatinase B and TIMP-2 is associated with progelatinase A. Malignant tumors many times exhibit complex patterns of expression of MMP's and TIMP's and therapeutic intervention might induce changes in this balance.

Using the in vitro protocol described in EXAMPLE 25 above, we have shown that the agents are potent inhibitors of MMP-9 activity in prostate cancer cells (PC-3) cells. MMP-2 activity is inhibited in DU-145 prostate cancer cell lines in vitro by the agents. This finding that the agents are potent inhibitors of MMP's activity clearly indicates an important new therapeutic function for the agents in cancer treatment.

To determine if the phosphonic acid agents were effective inhibitors of the MMP's of prostate cancer cells (PC3 and DU-145), cells were incubated in the presence of the different agents for 48 hours. Tissue samples were taken and subjected to zymography. Tissue samples were placed in glass homogenizers in a three fold weight/volume of lysis buffer consisting of 50 mM Tris-HCL, pH=7.4, with 200 mM sodium chloride and 0.1% Triton X-100. The samples were homogenized and centrifuged at 1500 g for 20 minutes. The supernatant was immediately analyzed by zymography. Protein content of each sample was determined by a modified Lowry method.

The expression of metalloproteinases 2 and 9 and tissue inhibitors of metalloproteinases (TIMP) 1 and 2 in human prostate tumor xenografts in nude mice is determined by the indirect immunoperoxidase method. Briefly, tissue sections are deparaffinized by 100% xylene and then hydrated with a graded series of ethanol. Frozen sections can also be utilized. The endogenous peroxidase is eliminated by incubation in 3% hydrogen peroxide for 30 minutes, and nonspecific binding of IgG to tissue protein blocked by incubation with 100% normal rabbit serum for 1 hour. The sections are then reacted with monoclonal anti-human gelatinase A (MMP-2) or B (MMP-9) antibody raised in mouse (Oncogene Research Products, 4° C. overnight. Biotinylated anti-mouse antibody is used as the secondary antibody followed by peroxidase-strepavidin complex. The slides are rinsed three times with PBS after each tetrahydrochloride and hematoxylin used for nuclear staining. Negative controls omitting either the primary or secondary antibodies are used for nonspecific staining. The ratio (%) of immunoreactive cells to total carcinoma cells is measured by counting cells in five different fields at X200. TIMPS's 1 and 2 are detected in frozen sections of the tumors using a monoclonal mouse antibody for human TIMP's and the Mouse Unitect Immunohistochemistry detection kit (Oncogene Research Products, Cambridge, Mass.).

EXAMPLE 27
Effect of the Phosphonic Acid Agents on Endothelial Cell Migration in vitro Suramin inhibits multiple control points of angiogenesis, such as angiogenic growth factors binding to endothelial cell surface, endothelial cell migration, proliferation and production of proteases (Coffey et al., 1987, Braddock et al., 1994, Pepper et al., 1994). Migration of microvascular endothelial cells is a key step in the angiogenesis process and appears to be more sensitive to suramin inhibition than does endothelial cell proliferation (Takano et al., 1994). Suramin significantly inhibited endothelial cell migration determined by both the number of cells that migrated and the distance traveled by the cells from the wound edge. The data confirmed that suramin inhibits microvascular endothelial cell migration in concentrations above 150 µg/ml and that the phosphonic acid agents are much more potent inhibitors of endothelial cell migration than suramin (10 to 30 times).

EXAMPLE 28
Effect of the Phosphonic Acid Agents on Tube Formation in Endothelial Cells in vitro Endothelial cell differentiation on Matrigel is a useful in vitro model for the study of certain steps in angiogenesis (Schnaper et al., 1993). The possibility that the phosphonic acid agents inhibit angiogenesis in vitro has been studied using Matrigel, a reconstituted matrix prepared from the Englebreth-Holm-Swarm (EHS) tumor extracellular matrix (Kleinman et al., 1982). When human umbilical vein endothelial cells or bovine microvascular endothelial cells were seeded onto Matrigel, they formed a network of capillary-like structures, mimicking the steps that occur during the formation of new microvessels. Thus, the culture of endothelial cells on Matrigel serves as a useful model for the study of endothelial cell activity during in vitro angiogenesis.

Although there is a dramatic morphologic change in endothelial cell population involving cell elongation, anastomosis and branching, gene transcription and translation are not required for the regulation of this process (Zimrin et al., 1995). Rather, post-translation-al events are involved since the Matrigel-dependent process could be inhibited by addition of a protein kinase inhibitor.

To measure the effect of the phosphonic acid agents on the ability of tube formation by human microvascular endothelial cells, 200 µl of Matrigel is plated on a 24 well culture plates. After the Matrigel is allowed to gel for 30 min at 37° C., 40,000 cells (previously grown on plastic dishes) in 1 ml MCDB-131 medium is plated onto the Matrigel. After 18 and 24 hr, the cultures are fixed, stained and the area of tubes formed on the surface of the Matrigel are quantitated using an image analysis system (Loats Associates, Inc., Westminster, Md.). Additional experiments need to be carried out in the presence of various amounts of PMA (40–200 ng/ml) to determine if the inhibitory effect of the phosphonic acid agents can be overcome by the stimulation of PKC with a phorbol ester.

The phosphonic acid agents inhibit tube formation in a dose-dependent manner and that stimulation of PKC by the phorbol ester might overcome the inhibition.

EXAMPLE 29
Antiangiogenic Effects of the Phosphonic Acid Agents Expressed in an in vivo Mammalian (Mouse) Model of Angiogenesis The phosphonic acid agents inhibit angiogenesis in a simple and rapid in vivo model that allows the ready quantitative assessment of angiogenic and antiangiogenic factors. The method developed by Passaniti et al. (1992) consists of subcutaneously injecting mice with bFGF embedded in Matrigel in the presence of heparin. Subcutaneous injection of Matrigel plus bFGF and heparin at the ventral midline achieved optimal and reproducible responses. Sprouts from vessels in the adjacent tissue penetrated the gel within 2 days, connecting it with the external vasculature and reaching a plateau after 4 days, and persisted up to 8 days. Matrigel forms a solid gel when injected into mice and support a rapid and intense angiogenic reaction in the presence of heparin and bFGF. Matrigel has been used to promote differentiation of endothelial cells into capillary structures in culture, and when utilized as a vehicle in vivo, may enhance the selectivity of endothelial cells entering the gel since basement membranes are not readily crossed by fibroblasts and other cells. Gels supplemented with bFGF and heparin induced intense vascularization. The site of injection and the age of the mice can affect the magnitude of the observed angiogenic response. Angiogenesis is quantitated by image analysis of vessels and by measuring the hemoglobin present in the vessels within the gel.

This approach is used to determine whether the selected phosphonic acid agents can inhibit angiogenesis in vivo using C57B1/6 mice (6 months old). All mice are treated on day 1 of the experimental protocol by injection of 0.2 ml of Matrigel with a dose of heparin plus bFGF shown to induce intense angiogenesis. The animals are also treated i.p. daily with 2.0, 0.2 and 0.05 nmoles/20 gram body weight of phosphonic acid agents shown to be active antiangiogenic compound in the CAM and HMEC1 all in vitro. The control group receives daily i.p. injections of physiological saline.

After five days of treatment, the mice are euthanized and dissected. Photographs are taken of the area around the Matrigel implants and the gel is removed along with a section of the peritoneal lining for support, typically the overlying skin. The Drabkin method (Drabkin reagent kit 525, Sigma, St Louis, Mo.) is used to measure hemoglobin levels in the implants. Protein content of the supernatant fluid is determined using the BioRad protein assay method. All specimens are fixed in 10% buffered formalin for at least 24 hr, dehydrated, embedded in paraffin and sectioned at 5 micron thickness, deparaffinized, and stained with hematoxylin and eosin. Selected sections are stained for Factor VIII-related antigen using an immunoperoxidase method. To measure the total area of neovessels, a computerized digitalyzer, the Optomax image analysis system (Optomax), is used.

The model described by Passaniti et al. (1992) is used as it gives ready quantitative assessment of angiogenesis and is reliable and shown to be useful in testing biological factors and drugs that regulate angiogenesis. Suramin is an effective inhibitor of angiogenesis in vivo as described by Pesenti et al. (1992). Furthermore, the active phosphonic acid agents are 10 to 30 times more active than suramin in inhibiting angiogenesis. Moreover, a direct correlation is found between the potency of inhibition of angiogenesis in the CAM assay and in the mouse model for the phosphonic acid analogues.

EXAMPLE 30

The compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of Formula I. The compounds are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the compounds can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixir.

Pharmaceutical compositions for parenteral and suppository administration can also be obtained using techniques standard in the art.

Another preferred use of the compounds is in a transdermal parenteral pharmaceutical preparation in a mammal such as a human. Accordingly, compositions suitable for administration to these areas are particularly included within the invention. The above parenteral solutions or suspensions may be administered transdermally and, if desired a more concentrated slow release form may be administered. Accordingly, incorporation of the active compounds in a slow release matrix may be implemented for administering transdermally. The compounds may be administered transdermally at about 1 to 20% of the composition and preferably about 5 to 15% wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy has so far been restricted to a limited number of drugs that possess the desirable physiochemical properties for diffusion across the skin barrier. One effective method of overcoming the barrier function of the skin is to include a penetration enhancer in the formulation of a transdermal therapeutic system. See Barry, Brian W.: Dermatological Formulations: Percutaneous Absorption (Dekker, New York, 1983); Bronough et al, Percutaneous Absorption, Mechanisms-Methodology-Drug Delivery, (Marcel Dekker, New York, N.Y. 1985); and Monkhouse et al, Transdermal drug deliver-problems and promises. Drug Dev. Ind. Pharm., 14, 183–209 (1988).

A penetration enhancer is a chemical compound that, when included in a formulation, temporarily increases the permeability of the skin to a drug allowing more of the drug to be absorbed in a shorter period of time. Several different types of penetration enhancers have been reported such as dimethylsulfoxide, n-decyl methyl sulfoxide, N,N-dimethylacetamide, N,N-dimethylformamide, 1-dodecylazacycloheptan-2-one (Azone), propylene glycol, ethanol, pyrrolidones such as N-methyl-2-pyrrrolidone (NMP) and surfactants. See Bronough et al, supra, and Stoughton et al, Azone: a New Non-toxic enhancer of percutaneous penetration. Drug Dev. Inc. Pharm., 9, 725–744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceuticals and is now under consideration for use in products intended for humans, Wells, D. A. et al: Disposition and Metabolism of Double-Labeled [$^3$H and $^{14}$C] N-methyl-2-pyrrolidone in the Rat. Drug Met. Disps., 16, 243–249 (1988). Animal and human experiments have shown very little irritation or sensitization potential. Ames type assays and chronic exposure studies have not revealed any significant toxicity, Wells et al, Mutagenicity and Cytotoxicity of N-methyl-2-p [yrrolidone and 4-(methyl amino) Butanoic Acid in the Salmonella/microsome Assay. J. Appl. Tox., 8, 135–139 (1988). N-methylpyrrolidone has also been shown to be an effective penetration enhancer. Barry et al, Optimization and Bioavailability of Topical Steroids: Penetration Enhancers Under Occlusion. J. Inv. Derm., 82, 49–52 (1984); Akter et al, Absorption Through human Skin of Ibuprofen and Flurbiprofen; Effect of Dose Variation, Deposited Drug Films, Occlusion and the Penetration Enhancer N-methyl-2-pyrrolidone. J. Pharm. Pharmacol., 37, 27–37 (1984); Hole-gaard et al, Vesical Effect on Topical Drug Delivery IV. Effect of N-methylpyrrolidone and Polar Lipids on Percutaneous Transport. Int. J. Pharm., 43, 233–240 (1988); Sugibayashi et al, Effect of Several Penetration Enhancers on the Percutaneous Absorption of Indomethacin in Hairless Rat. Chem. Pharm. Bull., 36, 1519–1529 (1988); Bennett et al, Optimization of Bioavailability of Topical Steroids: Non-occluded penetration Enhancers Under Thermodynamic Control. J. Pharm. Pharmacol., 37, 298–304 (1985); Sasaki et al, Enhancing Effect of Pyrrolidone Derivatives on Trans-derman Drug Delivery. 1. Ing. J. Pharm., 44, 14–24 (1988); Lee et al, Toxicity of N-methyl-2-pyrrolidone (NMP): Teratogenic, Subchronic and Two-year Inhalation Studies, Fund. Appl., Tox., 9, 222–235 (1987).

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a suramin compound is about 12 g administered for 6 weeks (NCI). The phosphonic acid agents may be administered in a dosage of about 3 g for 6 weeks.

Compounds of the present invention may be administered topically at about 1 to 20 wt % of the composition, and preferably about 5 to 15 wt %. Suramin is presently given by sterile i.v. injection because of the poor absorption from the gut. For suramin treatment of prostate cancer (Stein 1989), suramin is given i.v. (1–2 g/wk) for a 6 week treatment period. The chemical characteristics of the phosphonic acid agents suggest that higher effective dosages are achievable.
References Ades E W, Candal F J, Swerlick R A, et al. Establishment of an immortalized human microvascular endothelial cell line. J. Invest. Dermatol., 99:683, 1992.

Ausprunk D H, D R Knighton, J Folkman. Differentiation of vascular endothelium in the chick chorioallantois: a structural and autoradiographic study. Dev. Biol. 38:237–248, 1974.

Baghdiguian S, J A Boudier, J L Boudier, J Fantini. Autoradiographic localization of tritiated suramin in polarized human colon carcinoma cells. Cancer Lett. 75:151–156, 1993.

Behrendt N, E Ronne, K Dano. Binding of the urokinase-type plasminogen activator to its cell surface receptor is inhibited by low doses of suramin. J Biol Chem 268:5985–5989, 1993.

Bojanowski K, S Lelievre, J Markovits, J Couprie, A Jacquemin-Sablon, A K Larsen. Suramin is an inhibitor of DNA topoisomerase II in vitro and in Chinese hamster fibrosarcoma cells. Proc. Natl. Acad. Sci. USA 89:3025–3029, 1992.

Bojanowski K, O Filhol, C Cochet, E M Chambaz, A K Larsen. DNA topoisomerase II and casein kinase II associate in a molecular complex that is catalytically active. J Biol Chem 268:22920–22926, 1993.

Bojanowski K, K Nishio, M Fukuda, A K Larsen, N Saijo. Effect of suramin on p34cdc2 kinase in vitro and in extracts from human H69 cells: evidence for a double mechanism of action. Biochem Biophys Res Commun 203:1574–1580, 1994.

Bos O J M, E L M Vansterkenburg, J P Boon, M J Fischer, J Wilting, L H M Janssen. Location and characterization of the suramin binding sites of human serum albumin. Biochem Pharmacol., 40:1595, 1990.

Braddock P S, D E Hu, P D Fan, I J Stratford, A L Harris, R Bicknell. A structure activity analysis of antagonism of the growth factor and angiogenic activity of basic fibroblast growth factor by suramin and related polyanions. Br. J. Cancer 69:890–898, 1994.

Braunhut S J, L S Gudas, J Sasse P A D'Amore. Expression of FGF by F9 teratocarcinoma cells as a function of differentiation. J Cell Biol 108:2467–2476, 1989.

Brooks P C, Montgomery A P, Rosenfeld M, et al. Integrin-à and -á antagonists promote tumor regression by inducing apoptosis of angiogenic blood vessels. Cell, 79:1157–1164, 1994.

Carmichael J, W G DeGraff, A F Gazdar, J D Minna, J B Mitchell. Evaluation of tetrazolium-based semiautomated colorimetric assay: assessment of chemosensitivity testing. Cancer Res 47:936–942, 1987.

Coffey R J, E B Leof, G D Shipley, H L Moses. Suramin inhibition of growth factor receptor binding and mitogenicity in AKR-2B cells. J. Cell. Physiol. 132:143–148, 1987.

Craig K, S Mi, E O Harrington, J D Chang, S Mallette, J A Ware. Requirement for protein kinase C activation in basic fibroblast growth factor induced human endothelial cell proliferation. Circ. Res. 77:231–238, 1995.

Crum R, Szabo S, Folkman J. A new class of steroids inhibits angiogenesis in the presence of heparin or a heparin fragment. Science 230:1375–1378, 1985.

Defilippi P, C Bozzo, G Volpe, G Romano, M Venturino, L Silengo, G Tarone. Integrin-mediated signal transduction in human endothelial cells: analysis of tyrosine phosphorylation events. Cell Adhesion Commun 2:75–86, 1994.

Denekamp J. Vasculature as a target for tumor therapy. In: Hammersen F, Hudlicka O, ed., Progress in Applied Microcirculation. Basel:Karger, 4:28–38, 1984.

Ellis V, K Dano. Specific inhibition of the activity of the urokinase receptor-mediated cell-surface plasminogen activation system by suramin. Biochem J 296:505–510, 1993.

Flamme I, K Schulze-Osthoff, H J Jacob. Mitogenic activity of chicken chorioallantoic membrane fluid is temporally correlated to vascular growth in the chorioallantoic membrane and related to fibroblast growth factors. Development 11(3):683–690, 1991.

Foekens J A, A M Sieuwerts, E M J Stuurman-Smeets, H A Peters, J G M Klijn. Effects of suramin on cell-cycle kinetics of MCF-7 human breast cancer cells in vitro. Br J Cancer 67:232–236, 1993.

Folkman J. Angiogenesis—retrospect and outlook. In: Angiogenesis: Key Principles—Science—Technology—Medicine. Ed. by R. Steiner, P. B. Wiesz & R. Langer, Birkhauser Verlag Basel/Switzerland, 1992.

Folkman J. Tumor angiogenesis. Adv. Cancer Res. 43:175–203, 1985.

Gagliardi A R, Hennig B, Collins D C. Antiestrogens Inhibit Endothelial Cell Growth Stimulated By Angiogenic Growth Factors. Anti-Cancer Res., 16:1–6, 1996.

Gagliardi A R, H Hadd, D C Collins. Inhibition of angiogenesis by suramin. Cancer Res. 52:5073–5075, 1992.

Ghosh J, R A Miller. Suramin, an experimental chemotherapeutic drug, irreversibly blocks T cell CD45-protein tyrosine phosphatase in vitro. Biochem Biophys Res Commun 194:36–44, 1993.

Haller T, P Dietl, P Deetjen, H Volkl. The lysosomal compartment as intracellular calcium store in MDCK cells: a possible involvement in InsP3-mediated Ca2=release. Cell Calcium 19:157–165, 1996.

Jindal H K, C W Anderson, R G Davis, J K Vishwanatha. Suramin affects DNA synthesis in HeLa cells by inhibition of DNA polymerases. Cancer Res 50:7754–7757, 1990.

Kent K C, S Mii, E O Harrington, J D Chang, S Mallette, J A Ware. Requirement for protein kinase C activation in basic fibroblast growth factor-induced human endothelial cell proliferation. Circ Res 77:231–238, 1995.

Koide H, K Ogita, U Kikkawa, Y Nishizuka. Isolation and characterization of the E subspecies of protein kinase C from rat brain. Proc Natl Acad Sci USA 89:1149–1153, 1992.

LaBarca C, K Paigen. A simple, rapid and sensitive DNA assay procedure. Anal Biochem 102:344–352, 1980.

La Rocca R V, C A Stein, R Danesi, et al. Suramin, a novel antitumor compound. J Steroid Biochem Molec Biol 37:893–898, 1990.

Leavesley P I, M A Schwartz, M Rosenfeld, D A Cheresh. Integrin á1- and á3-mediated endothelial cell migration is triggered through distinct signaling mechanisms. J Cell Biol 121:163–170, 1993.

Mahoney C W, A Azzi, K-P Huang. Effects of suramin, an anti-human immunodeficiency virus reverse transcriptase agent, on protein kinase C. J Biol Chem 265:5424–5428, 1990.

Mattila P, M-L Majuri, S Tiisala, et al. Expression of six protein kinase C isotypes in endothelial cells. Life Sci 55:1253–1260, 1994.

Meredith J E, B Frazeli Jr, M A Schwartz. Adhesion to fibronectin stimulates isositol lipid synthesis and enhances PDGF-induced inositol lipid breakdown. J Cell Biol 121:673–678, 1993.

Middaugh C R, H Mach, C J Burke, D B Volkin, J M Dabora, P K Tsai, M W Bruner, J A Ryan, K E Marfia. Biochemistry 31:9016–9024, 1992.

Mitchen J, R Rago, G Wilding. Effects of suramin on the proliferation of primary epithelial cell cultures derived from normal, benign hyperplastic and cancerous human prostates. Prostate 22:75–89, 1993.

Montesano R, Orci L. Tumor-promoting phorbol ester induced angiogenesis in vitro. Cell 42:469–472, 1985.

Panetti T S, S A Wilcox, C Horzempa, P J Mc-Keown-Longo. ává5 Integrin receptor-mediated endocytosis of vitronectin is protein kinase C-dependent. J Biol Chem 270:18593–18597, 1995.

Passaniti A, R M Taylor, R Pili, Y Guo, P V Long, J A Haney, R R Pauly, D S Grant, G R Martin. Methods in laboratory investigation. A simple, quantitative method for assessing angiogenesis and antiangiogenic agents using reconstituted basement membrane, heparin, and fibroblast growth factor. Lab Invest 67:519, 1992.

Pepper M S, J-D Vassalli, J W Wilks, L Schweiger, L Orci, R Montesano. Modulation of bovine microvascular endothelial cell proteolytic properties by inhibitors of angiogenesis. J. Cell Biol. 55:419–434, 1994.

Pesenti E, F Sola, N Mongelli, M Grandi, F Spreafico. Suramin prevents neovascularization and tumor growth through blocking of basic fibroblast growth factor activity. Br. J. Cancer 66:367–372, 1992.

Pollak M and M Richard. Suramin blockade of insulin like growth factor 1 stimulated proliferation of human osteosarcoma cells. J Natl Cancer Inst. 82:1349–1352, 1990.

Qiao L, J G Pizzolo, M R Melamed. Effects of suramin on expression of proliferation associated nuclear antigens in DU-145 prostate carcinoma cells. Biochem Biophys Res Commun 201:581–588, 1994.

Re F, A Zanetti, M Sironi, N Polentarutti, L Lanfrancone, E Dejana, F Colotta. Inhibition of anchorage-dependent cell spreading triggers apoptosis in cultured human endothelial cells. J Cell Biol 127:537–546, 1994.

Reid S, Cross R, Snow E C. Combined Hoechst 33342 and merocyamine 540 staining to examine murine B cell cycle stage, viability and apoptosis. J Immunol Methods 1996, In press.

Ruoslahti E, J C Reed. Anchorage dependence, integrins and apoptosis. Cell 77:477–478, 1994.

Sastry S K, A F Horwitz. Integrin cytoplasmic domains: Mediators of cytoskeletal linkages and extra- and intracellular initiated transmembrane signaling. Curr Opin Cell Biol 5:819–831, 1993.

Schnaper H W, Kleinman H K, Grant D S. Role of laminin in endothelial cell recognition and differentiation. Kidney Int 43:20–25, 1993.

Schrell U M H, S Gauer, F Kiesewetter, A Bickel, J Hren, E F Adams, R Fahlbusch. Inhibition of proliferation of human cerebral meningioma cells by suramin: effects on cell growth, cell cycle phases, extracellular growth factors, and PDGF-BB autocrine growth loop. J Neurosurg 82:600–607, 1995.

Sriramarao P, M Mendler, M A Bourdon. Endothelial cell attachment and spreading on human tenascin is mediated by à2á1 and àvá3 integrins. J Cell Sciences 105:1001–1012, 1993.

Takano S, S Gately, M E Neville, W F Herblin, J L Gross, H Engelhard, M Perricone, K Eidsvoog, S Brem. Suramin, an anticancer and angio-suppressive agent inhibits endothelial cell binding of basic fibroblast growth factor, migration, proliferation and induction of urokinase-type plasminogen activator. Cancer Res 64:2654–2660, 1994.

Tsopanoglou N E, G C Haralabopoulos, M E Maragoudakin. Opposing effects on modulation of angiogenesis by protein kinase C and cAMP-mediated pathways. J. Vasc Res 31:195–204, 1994.

Vindelov L L, I J Christensen, N I Nissen. A detergent-trypsin method for the preparation of nuclei for flow cytometric DNA analysis. Cytometry 6:348–356, 1985.

Wei Y, M Lukashev, D I Simon, S C Bodary, S Rosenberg, M V Doyle, H A Chapman. Regulation of integrin function by the urokinase receptor. Science 273:1551, 1996.

Yamamura S, P R Nelson, K C Kent. Role of protein kinase C in attachment, spreading, and migration of human endothelial cells. J Surg Res 63:349–354, 1996.

Zimrin A B, B Villeponteau, T Maciag. Models of in vitro angiogenesis: endothelial cell differentiation on fibrin but not Matrigel is transcriptionally dependent. Biochem Biophys Res Commun 213:630–638, 1995.

Ausprunk D H, D R Knighton, J Folkman. Differentiation of vascular endothelium in the chick chorioallantois: a structural and autoradiographic study. Dev. Biol. 38:237–248, 1974.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All relevant portions of patents and publications cited herein are incorporated by reference in their entireties.

What is claimed is:

1. A phosphonic acid agent of the following formula:

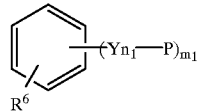

wherein

P is a phosphonic acid or a phosphonic acid substituted with one or more alkali metals;

Y is —OCO—, —NR$^1$CO—, or —CON(R$^1$)R$^2$—;

R$^1$ is H, CH$_2$CO$_2$H, or substituted or unsubstituted alkyl;

R$^2$ is substituted or unsubstituted alkylene;

$m_1$ is an integer from 2 to 4;

$n_1$ is 1, or 2;

R$^6$ is substituted or unsubstituted alkyl, or NCOR$^7$; and

R$^7$ is aryl, substituted aryl, or nitro substituted aryl.

2. The phosphonic acid agent according to claim 1, wherein $m_1$ is 2.

3. The phosphonic acid agent according to claim 1, wherein P is substituted with sodium or lithium.

4. The phosphonic acid agent according to claim 1, wherein $n_1$ is 1, $m_1$ is 2 and P is substituted with one or more alkali metals.

5. The phosphonic acid agent according to claim 1, wherein $n_1$ is 1, $m_1$ is 2, P is substituted with one or more alkali metals and R$^6$ is NCOR$^7$.

6. A pharmaceutical composition for the treatment of angiogenesis dependent conditions or tumors comprising an effective amount of a phosphonic acid agent of claim 1 and a pharmaceutically acceptable carrier.

7. A pharmaceutical composition for the treatment of angiogenesis dependent conditions or tumors comprising an effective amount of a phosphonic acid agent of claim 2 and a pharmaceutically acceptable carrier.

8. A pharmaceutical composition for the treatment of angiogenesis dependent conditions or tumors comprising an effective amount of a phosphonic acid agent of claim 3 and a pharmaceutically acceptable carrier.

9. A pharmaceutical composition for the treatment of angiogenesis dependent conditions or tumors comprising an effective amount of a phosphonic acid agent of claim 4 and a pharmaceutically acceptable carrier.

10. A pharmaceutical composition for the treatment of angiogenesis dependent conditions or tumors comprising an effective amount of a phosphonic acid agent of claim 5 and a pharmaceutically acceptable carrier.

* * * * *